United States Patent
Bassler et al.

(10) Patent No.: US 10,551,295 B2
(45) Date of Patent: Feb. 4, 2020

(54) DEVICES, CYTOMETERS, METHODS AND COMPUTER PROGRAM FOR PROVIDING INFORMATION ON AT LEAST ONE SEQUENCE

(71) Applicant: Fraunhofer-Gesellschaft zur Foerderung der angewandten Forschung e.V., Munich (DE)

(72) Inventors: Michael Bassler, Mainz (DE); Stephan Quint, Dortmund (DE)

(73) Assignee: Fraunhofer-Gesellschaft zur Foerderung der eingetragenen Forschung e. V., Munich (DE)

( * ) Notice: Subject to any disclaimer, the term of this patent is extended or adjusted under 35 U.S.C. 154(b) by 224 days.

(21) Appl. No.: 15/738,162

(22) PCT Filed: Jun. 23, 2016

(86) PCT No.: PCT/EP2016/064492
§ 371 (c)(1),
(2) Date: Dec. 20, 2017

(87) PCT Pub. No.: WO2016/207262
PCT Pub. Date: Dec. 29, 2016

(65) Prior Publication Data
US 2018/0172575 A1 Jun. 21, 2018

(30) Foreign Application Priority Data
Jun. 26, 2015 (DE) .................. 10 2015 110 316

(51) Int. Cl.
*G01N 15/14* (2006.01)
*G01N 21/64* (2006.01)
*G06F 17/15* (2006.01)

(52) U.S. Cl.
CPC ..... *G01N 15/1459* (2013.01); *G01N 15/1434* (2013.01); *G01N 21/64* (2013.01); *G06F 17/15* (2013.01); *G01N 2015/1447* (2013.01)

(58) Field of Classification Search
CPC ....... G01N 2015/1447; G01N 15/1459; G01N 15/1434; G01N 21/64; G06F 17/15
See application file for complete search history.

(56) References Cited

U.S. PATENT DOCUMENTS

| | | | | |
|---|---|---|---|---|
| 2005/0249226 A1* | 11/2005 | Kang | ............... | H04N 21/23406 370/412 |
| 2005/0249285 A1* | 11/2005 | Chen | ..................... | H04N 19/51 375/240.16 |

FOREIGN PATENT DOCUMENTS

EP 2211164 A1 7/2010

OTHER PUBLICATIONS

P. Kiesel, M. Bassler, M. Beck and N. Johnson, Spatially modulated fluorescence emission from moving particles, Appl. Phys. Lett., 2009, 94, p. 41107.

(Continued)

*Primary Examiner* — Shogo Sasaki
(74) *Attorney, Agent, or Firm* — 2SPL Patent Attorneys

(57) ABSTRACT

Embodiments relate to a device (20), a method and a computer program for providing information on at least one sequence, wherein the at least one sequence describes temporally successive signal states, comprising a device (10), a method and a computer program for a cytometer (100) for providing information on one or several cells in a medium in a channel and comprising a cytometer (100). The device (20) comprises an interface (22), which is configured to receive information on a number of the signal states. The device (20) a computational module (24) which is configured to generate a plurality of possible sequences based on the information on the number of the signal states. The (Continued)

computational module (24) is further configured to calculate for at least a subset of the possible sequences correlation functions between a sequence and at least a temporal scaling of the sequence, wherein a correlation function includes a main lobe and one or several side lobes. The computational module (24) is further configured to determine the at least one sequence based on the correlation functions, wherein the order of the signal states within the at least one sequence is selected such that a side lobe in a correlation function of the sequence comprising the at least one temporal scaling of the sequence is reduced as compared to a side lobe which may maximally be acquired in a correlation function by different arrangements of the signal states in the sequence, and to determine the information on the at least one sequence based on the at least one sequence and provide the same via the interface (22).

17 Claims, 42 Drawing Sheets

(56) References Cited

OTHER PUBLICATIONS

R. Turyn and S. Storer, On binary sequences, Proceedings of the American Mathematical Society 12, 394 (1961).
S. Mertens, Exhaustive search for low-autocorrelation binary sequences, Journal of Physics A: Mathematical and General 29, L473 (1996).
G. E. Cosxon and J.C. Russo, Efficient exhaustive search for optimal-peak-sidelobe binary codes, IEEE Transactions on Aerospace and Electronic Systems 41, 302 {2005).
P. Borewein, R. Ferguson, and J. Knauer, The merit factor problem, 2000.
C. J. Nunn and G. E. Coxson, Best-known autocorrelation peak sidelobe levels for binary codes of length 71 to 105, IEEE Transactions on Aerospace and Electronic Systems 44, 392 (2008).
S. K. Shanmugam, C. Mongredien, J. Nielsen, and G. Lachapelle, Design of short synchronization codes for use in future GNSS system, International Journal of Navigation and Observation vol. 2008, Article ID 246703.
Christian Sommer, Die Größenabhängigkeit der Gleichgewichtsgeschwindigkeit von Partikeln beim Transport Mikrokanälen, Dissertation Jul. 2014, Technische Universität Darmstadt.
Forster Roger: Manchester encoding: opposing definitions resolved, Engineering Science and Education Journal, vol. 9, 2000, No. 6, pp. 278-280, ISSN 0963-7346.
Kettlitz Siegfried W. et al, Particle detection from spatially modulated fluorescence Signals, Proceedings of SPIE, vol. 9129, 2014.
Kettlitz Siegfried W. et al, Sensitivity Improvement in Based Particle Detection; Cytometry A, vol. 85A, 2014.
Christian Sommer et al: "The equilibrium velocity of spherical particles in rectangular microfluidic channels for size measurement", Lab on a Chip, Bd. 14, Nr. 13, May 14, 2014 (May 14, 2014), p. 2319.
Cohen Marvin N. et al: "Minimum peak sidelobe pulse compression codes", IEE International Radar Conference, May 7, 1990 (May 7, 1990), pp. 633-638.
Hadinejad-Mahram H et al: "Binary and quadriphase sequences with optimal autocorrelation properties: a survey" IEEE Transactions on Information Theory, IEEE Press, USA, Bd. 49, Nr. 12, Dec. 31, 2003.
Gregory E. Coxson et al, Efficient Exhaustive Search for Binary Complementary Code Sets; Institute of Electrical and Electronics Engineers, 2013.
J. Lindner: Binary sequences up to length 40 with best possible autocorrelation function, Electronics Letters, Bd. 11, Nr. 21, Oct. 16, 1975.

* cited by examiner

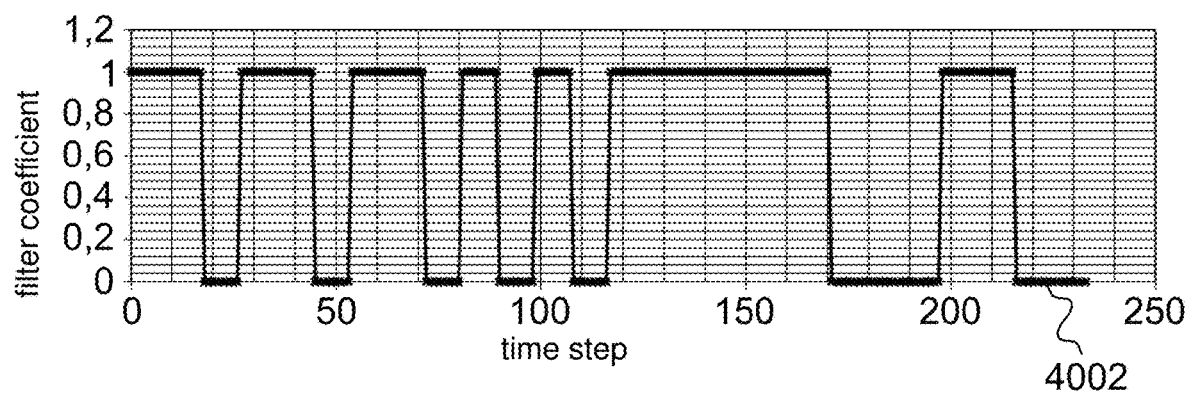
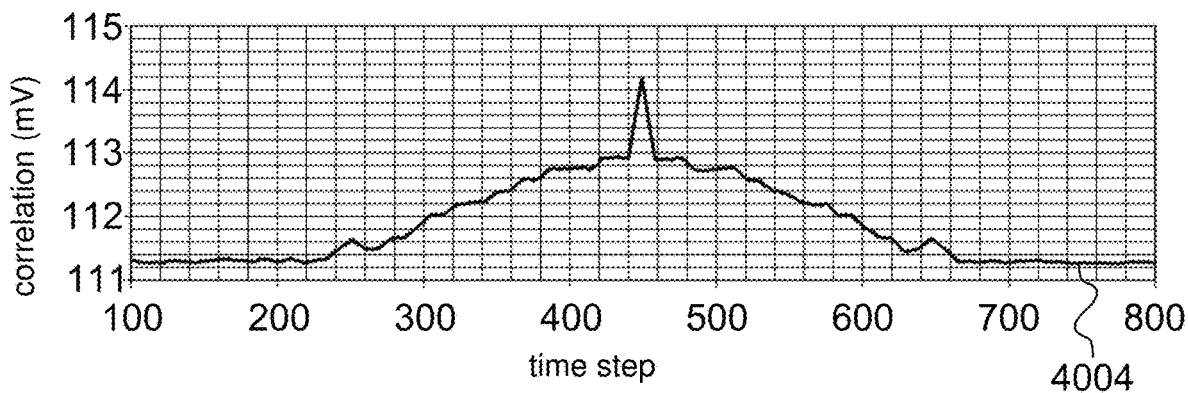
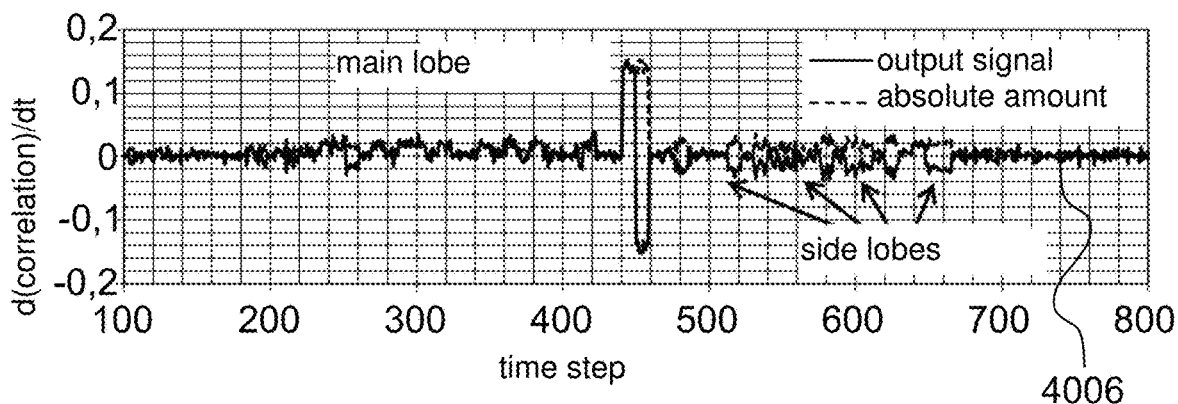
Fig. 4

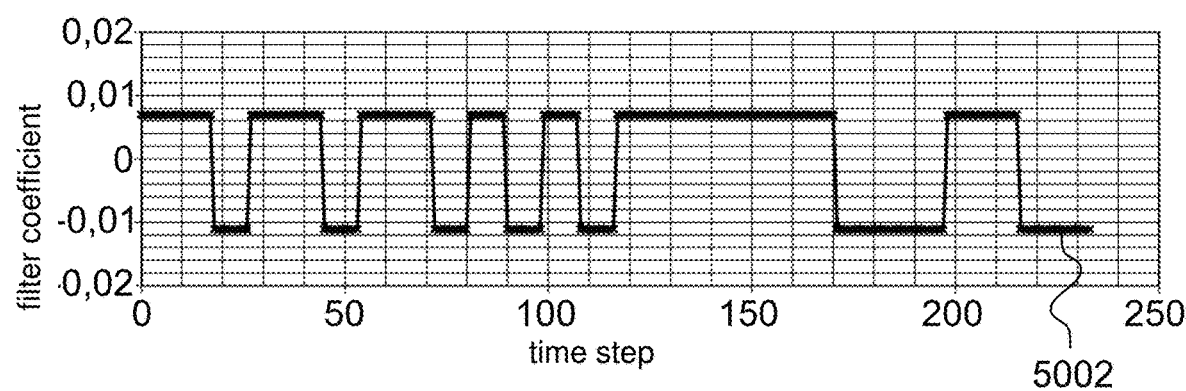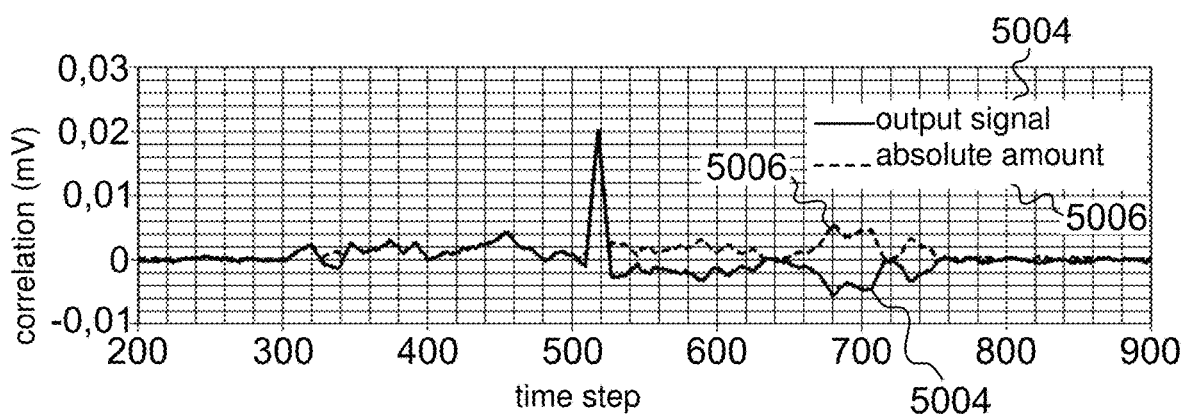
Fig. 5

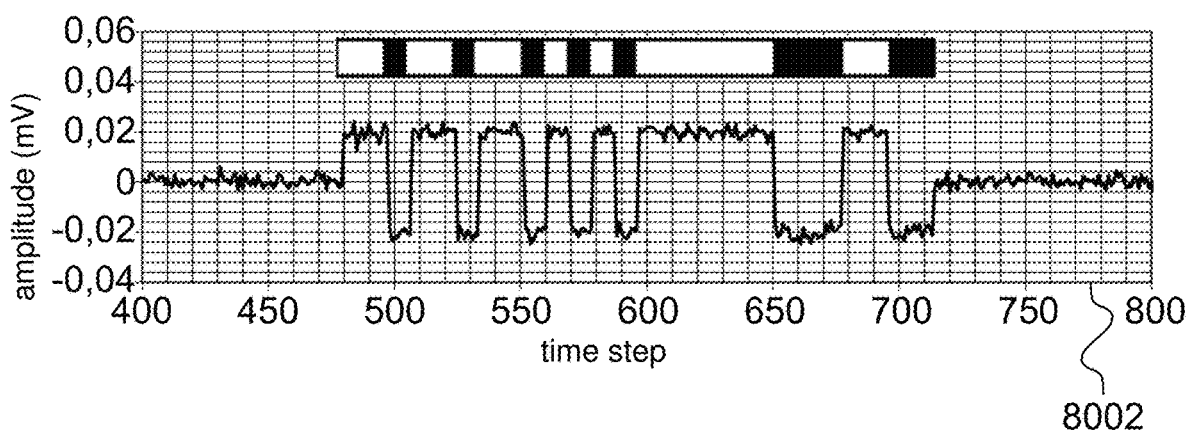
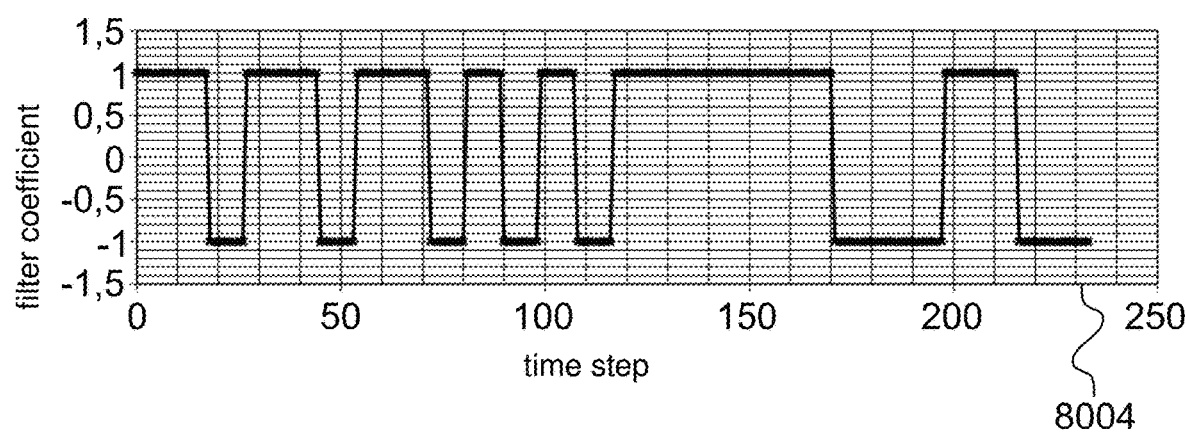
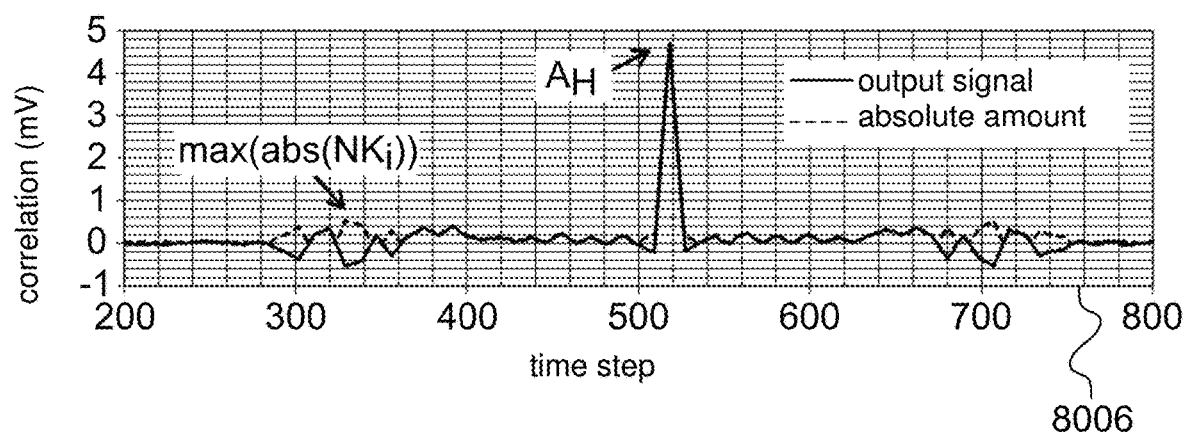
Fig. 8

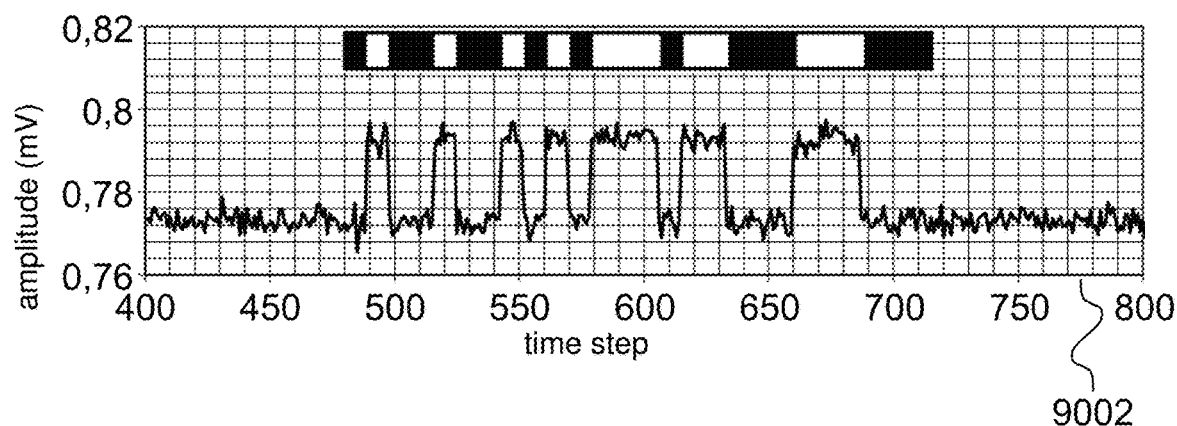
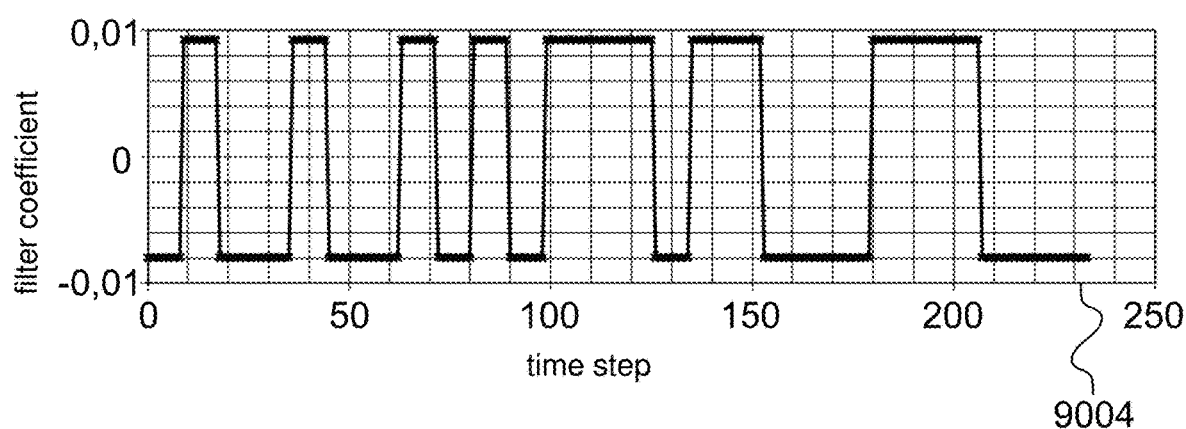
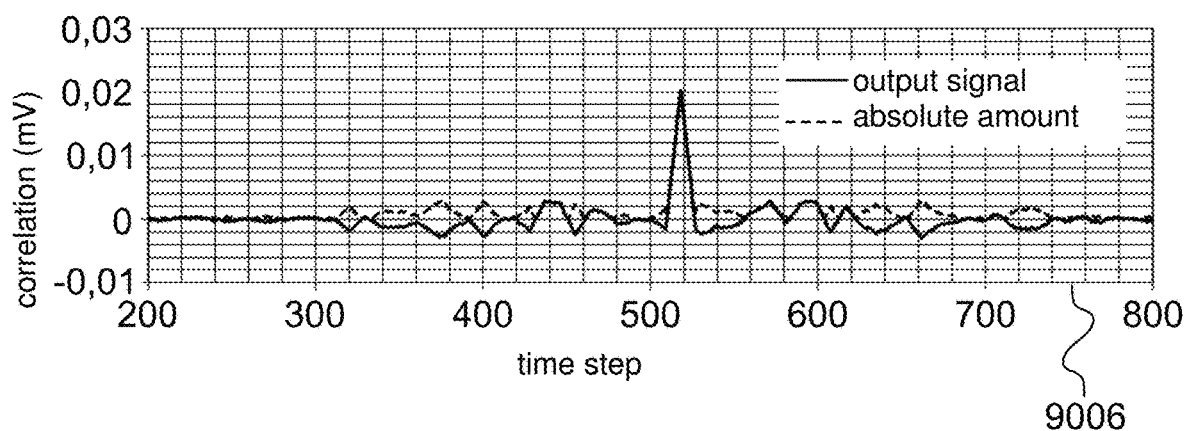
Fig. 9

| Code-ID | Code | L | E | SNRGain | Q1DI |
|---|---|---|---|---|---|
| ULABS-Q1D33(16,#1) | S1001001101010110001100110011111110000T | 33 | 16 | 2,87 | 978,8 |
| ULABS-Q1D32(13,#1) | S1000011100010010010011011101000000T | 32 | 13 | 2,78 | 870,9 |
| ULABS-Q1D31(13,#1) | S100001110001100100110101110100000T | 31 | 13 | 2,75 | 812,0 |
| ULABS-Q1D30(14,#1) | S10001100110010010101101011110000T | 30 | 14 | 2,73 | 806,2 |
| ULABS-Q1D29(10,#1) | S0001100011101000101011110000T | 29 | 10 | 2,56 | 752,3 |
| ULABS-Q1D28(13,#1) | S0011000111101011110101010100T | 28 | 13 | 2,64 | 761,6 |
| ULABS-Q1D27(13,#1) | S0100101101110111011111000100T | 27 | 13 | 2,60 | 635,8 |
| ULABS-Q1D26(14,#1) | S10101011101111110010001110T | 26 | 14 | 2,54 | 564,7 |
| ULABS-Q1D25(10,#1) | S1000100001111010010100100T | 25 | 10 | 2,45 | 513,7 |
| ULABS-Q1D24(10,#1) | S001100110100010101101000T | 24 | 10 | 2,42 | 505,9 |
| ULABS-Q1D23(10,#1) | S00101101001011001100T | 23 | 10 | 2,38 | 513,0 |
| ULABS-Q1D22(8,#1) | S0010110100100111100000T | 22 | 8 | 2,26 | 429,5 |
| ULABS-Q1D21(9,#1) | S010100001111011001000T | 21 | 9 | 2,27 | 397,2 |
| ULABS-Q1D20(9,#1) | S01010001111101100100T | 20 | 9 | 2,22 | 401,7 |
| ULABS-Q1D19(8,#1) | S10001000111101001000T | 19 | 8 | 2,15 | 331,1 |
| ULABS-Q1D18(7,#1) | S010001001111000010T | 18 | 7 | 2,07 | 300,2 |
| ULABS-Q1D17(4,#1) | S01010011001010000T | 17 | 4 | 1,75 | 237,9 |
| ULABS-Q1D16(4,#1) | S0000010100110000T | 16 | 4 | 1,73 | 249,4 |
| ULABS-Q1D15(8,#1) | S100110101011100T | 15 | 8 | 1,93 | 208,9 |
| ULABS-Q1D14(4,#1) | S00101010011000000T | 14 | 4 | 1,69 | 169,0 |
| ULABS-Q1D13(5,#1) | S010101110100T | 13 | 5 | 1,75 | 161,1 |
| ULABS-Q1D12(5,#1) | S0100101110001T | 12 | 5 | 1,71 | 151,9 |
| ULABS-Q1D11(5,#1) | S01001011100T | 11 | 5 | 1,65 | 105,4 |
| ULABS-Q1D10(4,#1) | S010100100T | 10 | 4 | 1,55 | 83,7 |
| ULABS-Q1D9(3,#1) | S00110100T | 9 | 3 | 1,41 | 67,9 |
| ULABS-Q1D8(3,#1) | S01011000T | 8 | 3 | 1,37 | 57,5 |

Fig. 11 (part 1)

| | | | | |
|---|---|---|---|---|
| LABS-Q1D40(16,#1) | S00001111000100101101011010010001001T | 40 | 16 | 3,10 | 1046,6 |
| LABS-Q1D39(16,#1) | S00111100111101000011010100010101001T | 39 | 16 | 3,07 | 597,1 |
| LABS-Q1D38(15,#1) | S00000000111100001110100101010010010T | 38 | 15 | 3,01 | 481,5 |
| LABS-Q1D37(15,#1) | S00011110001111000101010010101011001T | 37 | 15 | 2,99 | 401,5 |
| LABS-Q1D36(15,#1) | S00000000111100010010100100101001001T | 36 | 15 | 2,96 | 650,9 |
| LABS-Q1D35(14,#1) | S00001111000100101010001111001011001T | 35 | 14 | 2,90 | 383,7 |
| LABS-Q1D34(14,#1) | S00110011000000001111010100101010101T | 34 | 14 | 2,87 | 459,0 |
| LABS-Q1D33(15,#1) | S00000001101010100111001011010101010T | 33 | 15 | 2,86 | 363,8 |
| LABS-Q1D32(14,#1) | S00000001110001011001010101011000000T | 32 | 14 | 2,81 | 374,9 |
| LABS-Q1D31(18,#1) | S00110011001101010101010011010100100T | 31 | 18 | 2,75 | 583,6 |
| LABS-Q1D30(18,#1) | S01010111001101010101010111110000T | 30 | 18 | 2,68 | 425,5 |
| LABS-Q1D29(16,#1) | S00100101011100110110111110000110T | 29 | 16 | 2,68 | 497,9 |
| LABS-Q1D28(16,#1) | S01110011011011101110111011010010T | 28 | 16 | 2,62 | 565,6 |
| LABS-Q1D27(16,#1) | S01001011011011011011011000111T | 27 | 16 | 2,55 | 486,3 |
| LABS-Q1D26(10,#1) | S11001110000010101001001001000T | 26 | 10 | 2,48 | 315,3 |
| LABS-Q1D25(10,#1) | S00011110000001010101011001T | 25 | 10 | 2,45 | 286,0 |
| LABS-Q1D24(10,#1) | S11001110000010101010100001T | 24 | 10 | 2,42 | 294,6 |
| LABS-Q1D23(13,#1) | S01110001111101010101001001T | 23 | 13 | 2,38 | 270,5 |
| LABS-Q1D22(8,#1) | S00000100110101001011100T | 22 | 8 | 2,26 | 240,4 |
| LABS-Q1D21(8,#1) | S11000001100101111001001T | 21 | 8 | 2,23 | 243,9 |
| LABS-Q1D20(12,#1) | S10101110001111100100T | 20 | 12 | 2,19 | 148,9 |
| LABS-Q1D19(6,#1) | S01001000100011110000T | 19 | 6 | 2,03 | 271,6 |
| LABS-Q1D18(6,#1) | S00000101101001000100T | 18 | 6 | 2,00 | 212,9 |
| LABS-Q1D17(10,#1) | S00111110011010100110T | 17 | 10 | 2,03 | 201,1 |
| LABS-Q1D16(6,#1) | S00101101010010000001T | 16 | 6 | 1,94 | 150,2 |
| LABS-Q1D15(6,#1) | S11100010001010010T | 15 | 6 | 1,90 | 108,9 |
| LABS-Q1D14(4,#1) | S00001100100100T | 14 | 4 | 1,69 | 169,0 |
| LABS-Q1D13(4,#1) | S00001110010101T | 13 | 4 | 1,66 | 139,1 |

1116

Fig. 11 (part 2)

| | | | | |
|---|---|---|---|---|
| LABS-Q1DI12(4,#1) | S0110010100000T | 12 | 4 | 1,63 | 88,4 |
| LABS-Q1DI11(5,#1) | S0100100011111T | 11 | 5 | 1,65 | 62,7 |
| LABS-Q1DI10(4,#1) | S1010011000T | 10 | 4 | 1,55 | 59,1 |
| LABS-Q1DI9(3,#1) | S000101100T | 9 | 3 | 1,41 | 67,9 |
| LABS-Q1DI8(3,#1) | S0110100T | 8 | 3 | 1,37 | 35,1 |
| LABS-Q1DI7(3,#1) | S101100T | 7 | 3 | 1,31 | 26,9 |
| LABS-Q1DI6(1,#1) | S000010T | 6 | 1 | 0,91 | 45,6 |
| LABS-Q1DI5(1,#1) | S00010T | 5 | 1 | 0,89 | 28,6 |
| LABS-Q1DI4(1,#1) | S0001T | 4 | 1 | 0,87 | 15,6 |
| LABS-Q1DI3(1,#1) | S001T | 3 | 1 | 0,82 | 6,5 |

Fig. 11 (part 3)

| Code-ID | Code | L | E | SNRGain | Q1DI |
|---|---|---|---|---|---|
| ULABS-Q1DP33(10,#1) | S10001000011000110001101010010000001T | 33 | 10 | 2,64 | 242,5 |
| ULABS-Q1DP32(14,#1) | S10000110000100111111100101001010T | 32 | 14 | 2,81 | 227,3 |
| ULABS-Q1DP31(12,#1) | S10001000001101111100010010100001T | 31 | 12 | 2,71 | 193,4 |
| ULABS-Q1DP30(10,#1) | S10001100001100101101011010100000T | 30 | 10 | 2,58 | 258,2 |
| ULABS-Q1DP29(11,#1) | S10000000111011101001100010100T | 29 | 11 | 2,61 | 193,6 |
| ULABS-Q1DP28(9,#1) | S10010000011110100001000100T | 28 | 9 | 2,47 | 180,7 |
| ULABS-Q1DP27(9,#1) | S01000100001101011011000001000T | 27 | 9 | 2,45 | 198,4 |
| ULABS-Q1DP26(12,#1) | S01001001010110110011000111000T | 26 | 12 | 2,54 | 148,2 |
| ULABS-Q1DP25(6,#1) | S00001101000011001100000000T | 25 | 6 | 2,14 | 141,6 |
| ULABS-Q1DP24(6,#1) | S00001010000011001100000T | 24 | 6 | 2,12 | 171,8 |
| ULABS-Q1DP23(6,#1) | S00001010100001100110000T | 23 | 6 | 2,11 | 129,6 |
| ULABS-Q1DP22(6,#1) | S00001100110010001010000T | 22 | 6 | 2,09 | 98,2 |
| ULABS-Q1DP21(9,#1) | S10000110110111010110000010T | 21 | 9 | 2,27 | 117,6 |
| ULABS-Q1DP20(8,#1) | S00110001010101011000010T | 20 | 8 | 2,19 | 78,9 |
| ULABS-Q1DP19(7,#1) | S001000101011111000100T | 19 | 7 | 2,10 | 75,7 |
| ULABS-Q1DP18(10,#1) | S0001001011111001100T | 18 | 10 | 2,11 | 93,7 |
| ULABS-Q1DP17(5,#1) | S00001100100010000T | 17 | 5 | 1,88 | 67,6 |
| ULABS-Q1DP16(8,#1) | S10000111101100010T | 16 | 8 | 2,00 | 128,0 |
| ULABS-Q1DP15(4,#1) | S0000110010100000T | 15 | 4 | 1,71 | 51,8 |
| ULABS-Q1DP14(5,#1) | S100011010000001T | 14 | 5 | 1,79 | 44,8 |
| ULABS-Q1DP13(5,#1) | S10010111101001T | 13 | 5 | 1,75 | 43,9 |
| ULABS-Q1DP12(6,#1) | S1000111110010T | 12 | 6 | 1,73 | 62,4 |
| ULABS-Q1DP11(6,#1) | S100011100T | 11 | 6 | 1,65 | 30,3 |
| ULABS-Q1DP10(5,#1) | S100101100T | 10 | 5 | 1,58 | 39,5 |
| ULABS-Q1DP9(3,#1) | S00101000T | 9 | 3 | 1,41 | 12,7 |
| ULABS-Q1DP8(4,#1) | S01011100T | 8 | 4 | 1,41 | 22,6 |

Fig. 13 (part 1)

| | | | | |
|---|---|---|---|---|
| LABS-Q1DP40(16,#1) | S0000111100001001011011101001000100010001T | 40 | 16 | 3,10 | 111,5 |
| LABS-Q1DP39(16,#1) | S000000001101001100011101001010110010101T | 39 | 16 | 3,07 | 98,5 |
| LABS-Q1DP38(15,#1) | S0000000011110001011110010101001100110T | 38 | 15 | 3,01 | 90,4 |
| LABS-Q1DP37(16,#1) | S110100010111100011110010100100110000T | 37 | 16 | 3,01 | 69,4 |
| LABS-Q1DP36(15,#1) | S0001111110000110110100010010101010T | 36 | 15 | 2,96 | 127,4 |
| LABS-Q1DP35(14,#1) | S000000010010000111100111010100011100T | 35 | 14 | 2,90 | 79,9 |
| LABS-Q1DP34(14,#1) | S0011001100000000111100101101010101T | 34 | 14 | 2,87 | 66,9 |
| LABS-Q1DP33(15,#1) | S1000100100000001010110100111000001T | 33 | 15 | 2,86 | 71,5 |
| LABS-Q1DP32(12,#1) | S0000001010001010110001100111100000T | 32 | 12 | 2,74 | 58,3 |
| LABS-Q1DP31(18,#1) | S1010110110110110011001111110000T | 31 | 18 | 2,75 | 116,1 |
| LABS-Q1DP30(12,#1) | S100011000010100010010000001111T | 30 | 12 | 2,68 | 54,3 |
| LABS-Q1DP29(16,#1) | S001010110110110110110110001110T | 29 | 16 | 2,68 | 113,2 |
| LABS-Q1DP28(16,#1) | S011101011101101111011100010111T | 28 | 16 | 2,62 | 94,3 |
| LABS-Q1DP27(16,#1) | S110011100000010101010010100111T | 27 | 16 | 2,55 | 137,3 |
| LABS-Q1DP26(10,#1) | S0001110000010101010101011001T | 26 | 10 | 2,48 | 62,0 |
| LABS-Q1DP25(10,#1) | S10011001010010010010011001T | 25 | 10 | 2,45 | 61,2 |
| LABS-Q1DP24(10,#1) | S011100011110101010000011100T | 24 | 10 | 2,42 | 97,8 |
| LABS-Q1DP23(13,#1) | S1110001111001010101001001T | 23 | 13 | 2,38 | 51,2 |
| LABS-Q1DP22(8,#1) | S1011101100101010110000000T | 22 | 8 | 2,26 | 70,8 |
| LABS-Q1DP21(12,#1) | S0101000110000011011T | 21 | 12 | 2,27 | 36,3 |
| LABS-Q1DP20(8,#1) | S0100100010001110000T | 20 | 8 | 2,19 | 25,8 |
| LABS-Q1DP19(6,#1) | S00001111010101100T | 19 | 6 | 2,03 | 42,7 |
| LABS-Q1DP18(9,#1) | S00001110101100110T | 18 | 9 | 2,12 | 43,0 |
| LABS-Q1DP17(10,#1) | S0001111111010111001T | 17 | 10 | 2,03 | 58,8 |
| LABS-Q1DP16(6,#1) | S00000011100011010T | 16 | 6 | 1,94 | 21,5 |
| LABS-Q1DP15(6,#1) | S111001000010010T | 15 | 6 | 1,90 | 24,6 |
| LABS-Q1DP14(4,#1) | S000011001010100T | 14 | 4 | 1,69 | 42,3 |
| LABS-Q1DP13(4,#1) | S00001100110100T | 13 | 4 | 1,66 | 33,7 |

Fig. 13 (part 2)

| | | | | |
|---|---|---|---|---|
| LABS-Q1DP12(4,#1) | S0000011100101T | 12 | 4 | 1,63 | 26,1 |
| LABS-Q1DP11(5,#1) | S1110001010T | 11 | 5 | 1,65 | 18,3 |
| LABS-Q1DP10(4,#1) | S1010011000T | 10 | 4 | 1,55 | 13,9 |
| LABS-Q1DP9(3,#1) | S0001011100T | 9 | 3 | 1,41 | 12,7 |
| LABS-Q1DP8(3,#1) | S0110100T | 8 | 3 | 1,37 | 8,6 |
| LABS-Q1DP7(4,#1) | S1110010T | 7 | 4 | 1,31 | 7,5 |
| LABS-Q1DP6(1,#1) | S000010T | 6 | 1 | 0,91 | 22,8 |
| LABS-Q1DP5(1,#1) | S00010T | 5 | 1 | 0,89 | 14,3 |
| LABS-Q1DP4(1,#1) | S0001T | 4 | 1 | 0,87 | 7,8 |
| LABS-Q1DP3(1,#1) | S001T | 3 | 1 | 0,82 | 3,3 |

Fig. 13 (part 3)

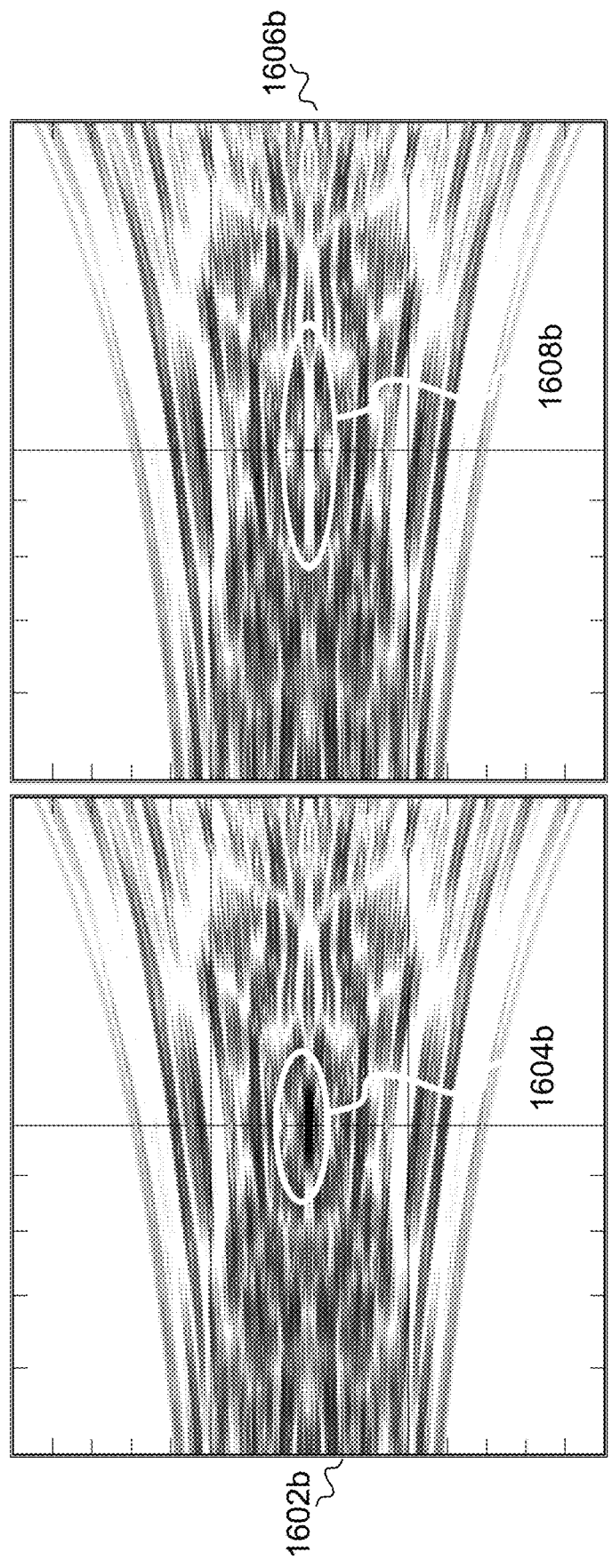
Fig. 16b

| Code-ID | Code | L | E | SNRGain | Q2DPs |
|---|---|---|---|---|---|
| ULABS-Q2DPs33(19,#1) | S00111001010111101011010100111100T | 33 | 19 | 2,84 | 28,9 |
| ULABS-Q2DPs32(16,#1) | S01001111010001011010101011100010T | 32 | 16 | 2,83 | 28,4 |
| ULABS-Q2DPs31(16,#1) | S00110010110010111101010110010100T | 31 | 16 | 2,78 | 29,3 |
| ULABS-Q2DPs30(15,#1) | S01011000100101110101010101011000T | 30 | 15 | 2,74 | 24,6 |
| ULABS-Q2DPs29(15,#1) | S00111010101010101010101010101100T | 29 | 15 | 2,69 | 26,8 |
| ULABS-Q2DPs28(14,#1) | S00101100100101010101011101101100T | 28 | 14 | 2,65 | 23,5 |
| ULABS-Q2DPs27(13,#1) | S01011000100101010101011111100100T | 27 | 13 | 2,60 | 23,1 |
| ULABS-Q2DPs26(10,#1) | S01000011010101010110000010T | 26 | 10 | 2,48 | 22,1 |
| ULABS-Q2DPs25(10,#1) | S00101011101010001011001000T | 25 | 10 | 2,45 | 22,0 |
| ULABS-Q2DPs24(11,#1) | S00101011101010010110101000T | 24 | 11 | 2,44 | 19,8 |
| ULABS-Q2DPs23(11,#1) | S00011010110101011101011000T | 23 | 11 | 2,40 | 18,9 |
| ULABS-Q2DPs22(11,#1) | S01010010111010101010111000T | 22 | 11 | 2,35 | 17,4 |
| ULABS-Q2DPs21(11,#1) | S01010010111010101010111100T | 21 | 11 | 2,29 | 17,3 |
| ULABS-Q2DPs209(9,#1) | S00101101010001010110100T | 20 | 9 | 2,22 | 14,9 |
| ULABS-Q2DPs19(11,#1) | S00111101010110100110100T | 19 | 11 | 2,15 | 14,4 |
| ULABS-Q2DPs18(8,#1) | S01010001101010110100T | 18 | 8 | 2,11 | 13,5 |
| ULABS-Q2DPs17(10,#1) | S00111101010101111100T | 17 | 10 | 2,03 | 14,7 |
| ULABS-Q2DPs16(7,#1) | S01110010101010010T | 16 | 7 | 1,98 | 11,7 |
| ULABS-Q2DPs15(5,#1) | S00011010101010000T | 15 | 5 | 1,83 | 10,6 |
| ULABS-Q2DPs14(4,#1) | S00001010010010000T | 14 | 4 | 1,69 | 10,6 |
| ULABS-Q2DPs13(7,#1) | S10010111010100T | 13 | 7 | 1,80 | 9,0 |
| ULABS-Q2DPs12(2,#1) | S00001010100000T | 12 | 2 | 1,29 | 8,1 |
| ULABS-Q2DPs11(2,#1) | S00001010100000T | 11 | 2 | 1,28 | 8,5 |
| ULABS-Q2DPs10(2,#1) | S00010101000T | 10 | 2 | 1,26 | 9,0 |
| ULABS-Q2DPs9(2,#1) | S00010101000T | 9 | 2 | 1,25 | 9,8 |
| ULABS-Q2DPs8(2,#1) | S00101010000T | 8 | 2 | 1,22 | 7,2 |

Fig. 19 (part 1)

| | | | |
|---|---|---|---|
| LABS-Q2DPs40(18,#1) | S001001000100011110111000111011101010101010T | 40 18 | 3,15 | 16,1 |
| LABS-Q2DPs39(21,#1) | S00100110011101000010110011110101010011100T | 39 21 | 3,11 | 14,3 |
| LABS-Q2DPs38(15,#1) | S000000011110000101010101010100110011110T | 38 15 | 3,01 | 12,4 |
| LABS-Q2DPs37(16,#1) | S1101010111110001101110010010000110000T | 37 16 | 3,01 | 12,2 |
| LABS-Q2DPs36(15,#1) | S0000000100110111001101010101010010010T | 36 15 | 2,96 | 15,4 |
| LABS-Q2DPs35(14,#1) | S000000011100010110010101010100011100T | 35 14 | 2,90 | 15,1 |
| LABS-Q2DPs34(15,#1) | S000000001110100011101010101010101001T | 34 15 | 2,90 | 9,8 |
| LABS-Q2DPs33(15,#1) | S00000011101011010011010101100110001T | 33 15 | 2,86 | 10,2 |
| LABS-Q2DPs32(20,#1) | S1111110101010010111001101101011001T | 32 20 | 2,74 | 11,1 |
| LABS-Q2DPs31(19,#1) | S11111110001110101100101010101010T | 31 19 | 2,71 | 10,8 |
| LABS-Q2DPs30(12,#1) | S11111100001110110111010011000100001T | 30 12 | 2,68 | 11,3 |
| LABS-Q2DPs29(16,#1) | S001001101101110110101110001110T | 29 16 | 2,68 | 10,9 |
| LABS-Q2DPs28(16,#1) | S011100001110111011110111010101010T | 28 16 | 2,62 | 11,4 |
| LABS-Q2DPs27(16,#1) | S01110001110110101010100011T | 27 16 | 2,55 | 10,9 |
| LABS-Q2DPs26(15,#1) | S0111000111111010101011100011110T | 26 15 | 2,52 | 6,8 |
| LABS-Q2DPs25(14,#1) | S011010101011111010110001000T | 25 14 | 2,48 | 5,0 |
| LABS-Q2DPs24(14,#1) | S001110001110011111010101010110T | 24 14 | 2,42 | 5,1 |
| LABS-Q2DPs23 9(9,#1) | S000100001001101101110100011T | 23 9 | 2,34 | 9,6 |
| LABS-Q2DPs22(8,#1) | S0000100010101010100111000T | 22 8 | 2,26 | 9,0 |
| LABS-Q2DPs21(13,#1) | S001111110011010101010110T | 21 13 | 2,23 | 9,7 |
| LABS-Q2DPs20(12,#1) | S1010110011011111100100T | 20 12 | 2,19 | 7,8 |
| LABS-Q2DPs19(6,#1) | S010010010001110000T | 19 6 | 2,03 | 6,5 |
| LABS-Q2DPs18(9,#1) | S100110111100001010T | 18 9 | 2,12 | 5,9 |
| LABS-Q2DPs17(7,#1) | S0001101001001010111T | 17 7 | 2,03 | 8,2 |
| LABS-Q2DPs16(6,#1) | S001101010010001001T | 16 6 | 1,94 | 8,3 |
| LABS-Q2DPs15(9,#1) | S000111011101101T | 15 9 | 1,90 | 6,1 |
| LABS-Q2DPs14(9,#1) | S1010110111111100T | 14 9 | 1,79 | 5,4 |
| LABS-Q2DPs13 4(4,#1) | S000001100101010T | 13 4 | 1,66 | 4,5 |

Fig. 19 (part 2)

| | | | | |
|---|---|---|---|---|
| LABS-Q2DPs12(4,#1) | S00000110010101T | 12 | 4 | 1,63 | 4,2 |
| LABS-Q2DPs11(5,#1) | S01001000111T | 11 | 5 | 1,65 | 3,7 |
| LABS-Q2DPs10(4,#1) | S00010100011T | 10 | 4 | 1,55 | 4,6 |
| LABS-Q2DPs9(3,#1) | S10010100T | 9 | 3 | 1,41 | 3,2 |
| LABS-Q2DPs8(3,#1) | S01101000T | 8 | 3 | 1,37 | 3,1 |
| LABS-Q2DPs7(3,#1) | S1011000T | 7 | 3 | 1,31 | 1,9 |
| LABS-Q2DPs6(2,#1) | S101000T | 6 | 2 | 1,15 | 4,6 |
| LABS-Q2DPs5(1,#1) | S00010T | 5 | 1 | 0,89 | 2,1 |
| LABS-Q2DPs4(1,#1) | S0010T | 4 | 1 | 0,87 | 1,9 |

Fig. 19 (part 3)

| Code-ID | Code | L | E | SNRGain | Q2DP |
|---|---|---|---|---|---|
| ULABS-Q2DP33(17,#1) | S100001110101010101010101101100001T | 33 | 17 | 2,87 | 30,7 |
| ULABS-Q2DP32(13,#1) | S010100100011101011001010110101000T | 32 | 13 | 2,78 | 29,7 |
| ULABS-Q2DP31(16,#1) | S001101001011101011101010101101100T | 31 | 16 | 2,78 | 29,3 |
| ULABS-Q2DP30(17,#1) | S010011110101101010101010101011100T | 30 | 17 | 2,71 | 26,0 |
| ULABS-Q2DP29(15,#1) | S000111010101010101010110101011000T | 29 | 15 | 2,69 | 26,8 |
| ULABS-Q2DP28(14,#1) | S010110010101010010110101011001100T | 28 | 14 | 2,65 | 23,8 |
| ULABS-Q2DP27(13,#1) | S010110001010101010101011110010T | 27 | 13 | 2,60 | 23,1 |
| ULABS-Q2DP26(10,#1) | S010001110101010101011000010T | 26 | 10 | 2,48 | 22,1 |
| ULABS-Q2DP25(10,#1) | S001010111010100001001011101000T | 25 | 10 | 2,45 | 20,8 |
| ULABS-Q2DP24(11,#1) | S001011011010101010101101000T | 24 | 11 | 2,44 | 19,8 |
| ULABS-Q2DP23(11,#1) | S000111011010101101010101000T | 23 | 11 | 2,40 | 19,5 |
| ULABS-Q2DP22(11,#1) | S010111001010110110101110100T | 22 | 11 | 2,35 | 17,7 |
| ULABS-Q2DP21(14,#1) | S010111011011011101010T | 21 | 14 | 2,16 | 17,9 |
| ULABS-Q2DP206(6,#1) | S100010100000101000001T | 20 | 6 | 2,05 | 16,1 |
| ULABS-Q2DP198(8,#1) | S100001101011010110001T | 19 | 8 | 2,15 | 15,5 |
| ULABS-Q2DP188(8,#1) | S001110101010010100T | 18 | 8 | 2,11 | 14,8 |
| ULABS-Q2DP17(10,#1) | S001110101010101100T | 17 | 10 | 2,03 | 14,7 |
| ULABS-Q2DP16(10,#1) | S010110101101110101T | 16 | 10 | 1,94 | 13,9 |
| ULABS-Q2DP15(9,#1) | S011011011010110T | 15 | 9 | 1,90 | 12,1 |
| ULABS-Q2DP14(4,#1) | S000101001010001T | 14 | 4 | 1,69 | 10,6 |
| ULABS-Q2DP13(7,#1) | S100101101001T | 13 | 7 | 1,80 | 9,3 |
| ULABS-Q2DP122(2,#1) | S000010100000T | 12 | 2 | 1,29 | 8,1 |
| ULABS-Q2DP11(7,#1) | S011011010T | 11 | 7 | 1,60 | 9,2 |
| ULABS-Q2DP10(2,#1) | S000101000T | 10 | 2 | 1,26 | 8,8 |
| ULABS-Q2DP9(2,#1) | S000101000T | 9 | 2 | 1,25 | 9,8 |
| ULABS-Q2DP8(2,#1) | S00101000T | 8 | 2 | 1,22 | 7,2 |

Fig. 21 (part 1)

| LABS-Q2DP40(18,#1) | S0010010001000110001111011000111010010101010T | 40 | 18 | 3,15 | 16,1 |
|---|---|---|---|---|---|
| LABS-Q2DP39(21,#1) | S00100110001101000101011110011100111100T | 39 | 21 | 3,11 | 14,3 |
| LABS-Q2DP38(15,#1) | S00000000111100001101010010100100110010T | 38 | 15 | 3,01 | 12,4 |
| LABS-Q2DP37(16,#1) | S110100001111011100010010001001100001T | 37 | 16 | 3,01 | 12,2 |
| LABS-Q2DP36(15,#1) | S0001111110001001100010010101010100010T | 36 | 15 | 2,96 | 15,4 |
| LABS-Q2DP35(14,#1) | S0000000100110110010010101010100011100T | 35 | 14 | 2,90 | 15,1 |
| LABS-Q2DP34(15,#1) | S000000001111001110010101010101011001T | 34 | 15 | 2,90 | 9,8 |
| LABS-Q2DP33(15,#1) | S000000001110101010010010001100110001T | 33 | 15 | 2,86 | 10,2 |
| LABS-Q2DP32(20,#1) | S1111111001010101001001100011001011001T | 32 | 20 | 2,74 | 11,1 |
| LABS-Q2DP31(19,#1) | S1111110001110010101010000110010111010T | 31 | 19 | 2,71 | 10,8 |
| LABS-Q2DP30(12,#1) | S111100001111011110110001000110001T | 30 | 12 | 2,68 | 11,3 |
| LABS-Q2DP29(16,#1) | S00100110110110110111011010111001110T | 29 | 16 | 2,68 | 10,9 |
| LABS-Q2DP28(16,#1) | S0111000011110011101110110111011010101T | 28 | 16 | 2,62 | 11,4 |
| LABS-Q2DP27(16,#1) | S00110001111011011111010101011000111T | 27 | 16 | 2,55 | 10,9 |
| LABS-Q2DP26(13,#1) | S0000001110011011010101010101101T | 26 | 13 | 2,55 | 6,2 |
| LABS-Q2DP25(14,#1) | S0110101001110111111001110001000T | 25 | 14 | 2,48 | 5,0 |
| LABS-Q2DP24(14,#1) | S001100010001110101011110110110T | 24 | 14 | 2,42 | 5,1 |
| LABS-Q2DP23(9,#1) | S0001000010010101010100011T | 23 | 9 | 2,34 | 9,6 |
| LABS-Q2DP22(8,#1) | S00000100110110101001110001T | 22 | 8 | 2,26 | 9,0 |
| LABS-Q2DP21(8,#1) | S1100000011001101010101001T | 21 | 8 | 2,23 | 9,6 |
| LABS-Q2DP20(12,#1) | S1010111001111110010010T | 20 | 12 | 2,19 | 7,0 |
| LABS-Q2DP19(6,#1) | S010010010010110100T | 19 | 6 | 2,03 | 6,5 |
| LABS-Q2DP18(6,#1) | S0000010110100001010T | 18 | 6 | 2,00 | 5,9 |
| LABS-Q2DP17(7,#1) | S000011100010101011T | 17 | 7 | 2,03 | 8,2 |
| LABS-Q2DP16(6,#1) | S001011010001001T | 16 | 6 | 1,94 | 8,3 |
| LABS-Q2DP15(9,#1) | S000111011011101T | 15 | 9 | 1,90 | 6,1 |
| LABS-Q2DP14(4,#1) | S00000110010100T | 14 | 4 | 1,69 | 5,4 |
| LABS-Q2DP13(4,#1) | S000001100101010T | 13 | 4 | 1,66 | 4,8 |

Fig. 21 (part 2)

| LABS-Q2DP12(4,#1) | S00000110010101T | 12 | 4 | 1,63 | 4,4 |
| LABS-Q2DP11(5,#1) | S01001000111T | 11 | 5 | 1,65 | 3,7 |
| LABS-Q2DP10(4,#1) | S00010100011T | 10 | 4 | 1,55 | 4,6 |
| LABS-Q2DP9(3,#1) | S000011010T | 9 | 3 | 1,41 | 3,3 |
| LABS-Q2DP8(3,#1) | S01101000T | 8 | 3 | 1,37 | 3,1 |
| LABS-Q2DP7(3,#1) | S1011000T | 7 | 3 | 1,31 | 1,9 |
| LABS-Q2DP6(2,#1) | S101000T | 6 | 2 | 1,15 | 4,3 |
| LABS-Q2DP5(1,#1) | S00010T | 5 | 1 | 0,89 | 1,6 |
| LABS-Q2DP4(1,#1) | S0010T | 4 | 1 | 0,87 | 1,9 |

Fig. 21 (part 3)

DEVICES, CYTOMETERS, METHODS AND COMPUTER PROGRAM FOR PROVIDING INFORMATION ON AT LEAST ONE SEQUENCE

TECHNICAL FIELD

Embodiments relate to a device, a method and a computer program for providing information on at least one sequence, to a device, a method and a computer program for a cytometer for providing information on one or several cells in a medium in a channel and to a cytometer.

BACKGROUND

In medical and biological research and in the analysis and detection of diseases many findings are based on analyzing cells. For the analysis of large quantities of cell, frequently flow cytometers are used. In a flow cytometer cells are conducted through a channel in a solution with high speed. These cells emit an optical signal, for example triggered by a light source, like e.g. a laser. This optical signal is detected by the flow cytometer and enables a determination of the characteristics of the cells in the solution, like e.g. the number of certain cell types or their size and other characteristics.

A further development of flow cytometry is based on the principle of the spatially modulated fluorescence (RMF; Räumlich Modulierte Fluoreszenz). In conventional flow cytometers the channel in which the solution with the cells is guided past the sensor is narrowed so that the cells pass the sensor individually. Here, highly precise optics are required for the detector and the laser for exciting and detecting the individual cells which require a complex setup and high space requirement of the flow cytometer. Flow cytometers which are based on the principle of spatially modulated frequencies may, however, simultaneously support the flow of several cells, for example in case of a lower complexity of the optical setup. The cells in the solution in the channel are excited simultaneously, for example by a laser, and the emitted light is influenced by a spatial filter, like a filter mask. The spatial filter provides for the sensor to detect a signal based on the filter for each excited cell. By an analysis of the signal which may be superposed by other cells, the cytometer may determine a number, speed and other characteristics of the cells in the solution. The quality of detection of the cells and cell characteristics is here based on the filter which may, for example, be described by a sequence of temporally successive signal states.

Further information may, for example, be found in the following documents:

P. Kiesel, M. Bassler, M. Beck and N. Johnson, Appl. Phys. Lett., 2009, 94, p. 41107;
N. Levanon and E. Mozeson, Radar Signals, Wiley, New York, 2004;
R. Turyn and S. Storer, On binary sequences, Proceedings of the American Mathematical Society 12, 394 (1961);
S. Mertens, Exhaustive search for low-autocorrelation binary sequences, Journal of Physics A: Mathematical and General 29, L473 (1996);
G. E. Coxson and J. C. Russo, E cient exhaustive search for optimal-peak-sidelobe binary codes, IEEE Transactions on Aerospace and Electronic Systems 41, 302 (2005);
P. Borewein, R. Ferguson, and J. Knauer, The merit factor problem, 2000;
C. J. Nunn and G. E. Coxson, Best-known autocorrelation peak sidelobe levels for binary codes of length 71 to 105, IEEE Transactions on Aerospace and Electronic Systems 44, 392 (2008); and
S. K. Shanmugam, C. Mongrédien, J. Nielsen, and G. Lachapelle, Design of short synchronization codes for use in future GNSS system, International Journal of Navigation and Observation 2008 (2008), Article ID 246703.

It is thus the object to find sequences using which the detection of cells may be improved. This object is solved by a device, a method and a computer program for providing information on at least one sequence.

SUMMARY

Embodiments are based on the finding that sequences which are used in a cytometer which is based on RMF comprise advantageous characteristics if they do not only comprise side lobes reduced in an autocorrelation function or correlation function with an amplitude-scaled variant, but also side lobes which are reduced in cross-correlation functions of the sequence with a temporal scaling of the sequence. The reduction of the side lobes of the cross-correlation function may here enable an improved detection of differently fast cells. Embodiments may further be based on the finding that sequences which are used in a cytometer which is based on RMF comprise advantageous characteristics if they are unipolar and/or if the correlation functions are determined based on balanced filters.

Embodiments provide a device for providing information on at least one sequence. The at least one sequence describes temporally successive signal states. The device includes an interface which is implemented to receive information on a number of the signal states. The device further includes a computational module which is implemented to generate a plurality of possible sequences based on the information on the number of signal states. The computational module is further implemented to calculate correlation functions between a sequence and at least a temporal scaling of the sequence for at least a subset of the possible sequences. A correlation function includes a main lobe and one or several side lobes. The computational module is further implemented to determine at least one sequence based on the correlation functions. The sequence of the signal states within the at least one sequence is selected such that a side lobe in a correlation function of the sequence comprising the at least one temporal scaling of the sequence is reduced as compared to a side lobe which may maximally be acquired in a correlation function by different arrangements of the signal states in the sequence. The computational module is further implemented to determine the information on the at least one sequence based on the at least one sequence and provide the same via the interface. The at least one sequence may be utilized in embodiments to improve the detection of temporally-scaled signals by means of a filter bank and to reduce side lobes of a correlation function of a received sequence and temporally scale sequences and thus reduce erroneous detections.

In some embodiments, the computational module may be implemented to determine the at least one sequence based on the correlation functions. The sequence of the signal states within the at least one sequence may be selected such that a sum based on the side lobes of a correlation function of the sequence comprising the at least one temporal scaling of the sequence is reduced as compared to a sum which may maximally be acquired by different arrangements of the signal states in the sequence, wherein the sum is based on side lobes resulting from the different arrangement. The sequence of the signal states within the at least one sequence may be selected such that a greatest side lobe in the correlation function of the sequence comprising the at least one temporal scaling of the sequence is reduced as compared to a greatest side lobe which may maximally be acquired by different arrangements of the signal states in the sequence. A reduction of a sum which is based on the side lobes of a correlation function of the sequence comprising the at least one temporal scaling of the sequence may, for example, reduce a noise floor in the correlation analysis in the detection by means of a filter bank and/or result in a lower erroneous detection rate in case of very noisy signals, as an overall energy is lower in the side lobes than in sequences which are optimized with respect to a reduction of the highest side lobe. A reduction of the highest side lobe may, for example, reduce erroneous detections in the detection by means of a filter bank and/or may enable the use of lower threshold values, i.e. a higher sensitivity, with the same error rate.

In at least some embodiments, the computational module may be implemented to determine the at least one sequence so that the sum which is based on the side lobes is below a first threshold value. The computational module may be implemented to determine the at least one sequence so that the highest side lobe is below a second threshold value. In embodiments, the first and/or the second threshold value may be used to accelerate a determination of the sequence and/or to evaluate certain sequences.

In some embodiments, the first threshold value may correspond to a second-lowest sum which is based on the side lobes of the correlation functions. The second threshold value may correspond to a greatest side lobe of a sequence with a second-lowest greatest side lobe of the correlation functions. By selecting the second-lowest sum and the second-lowest greatest side lobe as the first and second threshold value, determining a sequence whose correlation function results in a lowest sum or a lowest greatest side lobe may be enabled, for example also recursively.

In at least some embodiments, the computational module may be implemented to determine cleaned-up correlation functions based on the correlation functions. The computational module may be implemented to reduce an amount of main lobes in the cleaned-up correlation functions. The computation module may be implemented to determine the information on the at least one sequence based on the cleaned-up correlation functions. Reducing the amount of main lobes in the cleaned-up correlation functions may facilitate an analysis of the one or several side lobes and may correspond to a detection and reduction of the main lobes in a cytometer.

In some embodiments, the computational module may be implemented to determine a greatest main lobe among the main lobes of the correlation functions. The computational module may be implemented to reduce the contribution of main lobes in the cleaned-up correlation functions across the temporal extension of the greatest main lobe. A reduction of the contribution of the main lobes across the temporal extension of the main lobe may be easier to implement numerically.

In some embodiments, the computational module may be implemented to determine the contributions of the main lobes in the cleaned-up correlation functions of the temporally-scaled sequence and neighboring temporal scalings of the sequence and reduce the same based on a temporal position of the greatest main lobe and based on the correlation function of the temporally-scaled sequence including the greatest main lobe. By reducing the contributions of the main lobes in the cleaned-up correlation functions of the temporally-scaled sequence and neighboring temporal scalings of the sequence, for example, a more exact isolation of the main lobes may be acquired and double events may be supported.

In at least some embodiments, a sequence may comprise an average structural size. A structural size may be based on a number of equal successive signal states. The computational module may be implemented to generate the plurality of possible sequences based on a target area for the average structural size. The computational module may be implemented to determine the subset of possible sequences based on the average structural size and/or the target area for the average structural size. A determination of the subset of the possible sequences based on the average structural size may, for example, accelerate a determination of the at least one sequence and reduce a computational effort for determining the at least one sequence.

In at least some embodiments, the average structural size may correspond to an average of the structural sizes of a sequence. The target area for the average structural size may, for example, be between 1.3 and 1.8. A determination of the subset of the possible sequences based on the average structural size and the target area may, for example, accelerate determining the at least one sequence and reduce a computational effort for determining the at least one sequence.

In at least some embodiments, the computational module may be implemented to determine the plurality of possible sequences as unipolar sequences. By using unipolar sequences, an improved ratio of main lobe to side lobes may be acquired.

In some embodiments, a sequence may correspond to a binary sequence. The binary sequence may describe temporally equidistant successive signal states. The use of a binary sequence may, for example, enable a simple notation of the sequence.

Embodiments further provide a device for a cytometer. The device is implemented for providing information on one or several cells in a medium in a channel. The device includes a sensor module which is implemented to detect a filtered signal. The filtered signal is influenced by the cells streaming through the channel. The device further includes a filter which is implemented to spatially map a given sequence and which is implemented to provide the filtered signal based on the sequence and on a signal influenced by the cells streaming through the channel. The device further includes a control module which is implemented to provide the information on the one or several cells based on a correlation analysis of the detected filtered signal and at least one temporal scaling of the sequence. The sequence describes temporally successive signal states. The sequence of the signal states within the sequence is selected such that a side lobe in a correlation function of the sequence comprising the at least one temporal scaling of the sequence is reduced as compared to a side lobe which may maximally be acquired in the correlation function by different arrangements of the signal states in the sequence. The sequence may be used in embodiments to improve the detection of temporally-scaled signals by means of a filter bank which may, for example, be included in the control module and to reduce side lobes of a correlation function of a received sequence and temporally-scaled sequences and consequently reduce erroneous detections.

In some embodiments, a sequence of the signal states within the at least one sequence may be selected such that a sum which is based on side lobes of the correlation function of the sequence comprising the at least one temporal scaling of the sequence is reduced as compared to a sum which may maximally be acquired by different arrangements of the signal states in the sequence, wherein the sum is based on side lobes resulting from the different arrangements. The sequence of the signal states within the at least sequence may be selected such that a greatest side lobe of the correlation function of the sequence comprising the at least one temporal scaling of the sequence is reduced as compared to a greatest side lobe which may maximally be acquired by different arrangements of a signal state in the sequence. Reducing a sum which is based on the side lobes of a correlation function of the sequence comprising the at least one temporal scaling of the sequence may, for example, reduce a noise floor in the correlation analysis in the detection by means of a filter bank. Reducing a highest side lobe may, for example, reduce erroneous detections in the detection by means of a filter bank.

In some embodiments, the sum which is based on the side lobes may be below a first threshold value. The greatest side lobe may be below a second threshold value. In embodiments, the first and/or the second threshold value may be used to accelerate a determination of the sequence and/or to evaluate certain sequences.

In at least some embodiments, the first threshold value may correspond to a second-lowest sum which is based on side lobes of correlation functions of possible sequences. The second threshold value may correspond to a greatest side lobe of a sequence comprising a second-lowest greatest side lobe of the correlation function. By selecting the second-lowest sum and the second-lowest greatest side lobe as the first and second threshold value, determining a sequence may be enabled whose correlation function results in a lowest sum or a lowest greatest side lobe, for example also recursively.

In some embodiments, the sequence may correspond to a unipolar sequence. By using a unipolar sequence, an improved ratio of main lobe to side lobes may be acquired.

Embodiments further provide a cytometer including the device and a channel. The device is implemented to provide information on one or several cells in a medium in the channel to the cytometer. The device using the sequence may be utilized in embodiments to improve the detection of temporally-scaled signals, like e.g. optical signals of the cells in the channel, by means of a filter bank which may, for example, be included in the control module of the device and to reduce side lobes of a correlation function of a received sequence and to reduce temporally-scaled sequences and thus reduce erroneous detection.

Embodiments further provide a method for providing information on at least one sequence. The at least one sequence describes temporally successive signal states. The method includes obtaining information on a number of the signal states. The method further includes generating a plurality of possible sequences based on the information on the number of the signal states. The method further includes calculating correlation functions between a sequence and at least a temporal scaling of the sequence for at least one subset of the possible sequences. One correlation function includes a main lobe and one or several side lobes. The method further includes determining the at least one sequence based on the correlation functions. The series of the signal states within the at least one sequence is selected such that a side lobe in a correlation function of the sequence comprising the at least one temporal scaling of the sequence is reduced as compared to a side lobe which may maximally be acquired in a correlation function by different arrangements of the signal states in the sequence. The method further includes determining the information on the at least one sequence based on the at least one sequence and providing the information on the at least one sequence.

Embodiments further provide a method for providing information on one or several cells in a medium in a channel. The device includes detecting a filtered signal. The filtered signal is influenced by cells streaming through the channel. The method further includes providing the filtered signal based on a predetermined sequence, a signal influenced by cells streaming through the channel and a spatial mapping of the sequence. The method further includes providing the information on the one or several cells based on a correlation analysis of the detected filtered signal and at least one temporal scaling of the sequence. The sequence describes temporally successive signal states. The series of the signal states within the sequence is selected such that a side lobe in a correlation function of the sequence comprising the at least one temporal scaling of the sequence is reduced as compared to a side lobe in the correlation function which may maximally be acquired by different arrangements of the signal states in the sequence.

A further embodiment is a computer program for executing at least one of the above-mentioned methods when the computer program is executed on a computer, a processor or a programmable hardware component. A further embodiment is also a digital storage medium which is machine or computer-readable and comprises electronically readable control signals which may cooperate with a programmable hardware component so that one of the above-mentioned methods is executed.

BRIEF DESCRIPTION OF THE DRAWING

In the following, further advantageous implementations are described in more detail with reference to the embodiments illustrated in the Figures, to which embodiments are not restricted, however.

FIG. 4 shows a filter and a correlation signal comprising main peak, direct component and low-frequency component;

FIG. 5 shows a balanced filter for a sequence LABS26 and output signal comprising main lobe and side lobes;

FIG. 8 shows for the sequence LABS26 a bipolar DC free signal, a filter component and an output signal;

FIG. 9 shows a unipolar signal with DC component, a filter component and an output signal for the sequence Q1DP26(12,#1);

FIG. 11 shows the respectively best examined sequences from a class of LABS and ULABS assessed according to a quality index number Q1D1 in one exemplary embodiment;

FIG. 13 shows the respectively best sequences of a class of LABS and ULABS assessed according to a quality index number Q1DP in one exemplary embodiment;

FIGS. 16a and 16b show cutting out the main lobes for determining the cleaned-up correlation function in embodiments as an example for ULABS-Q2DPs31(16,#1);

FIG. 19 shows an exemplary list of the respectively best examined sequences of the class of LABS and ULABS assessed according to the quality index number Q2DPs;

FIG. 21 shows an exemplary list of the respectively best examined codes from class LABS and ULABS assessed according to the quality index number Q2DP;

DESCRIPTION

Figure 1:
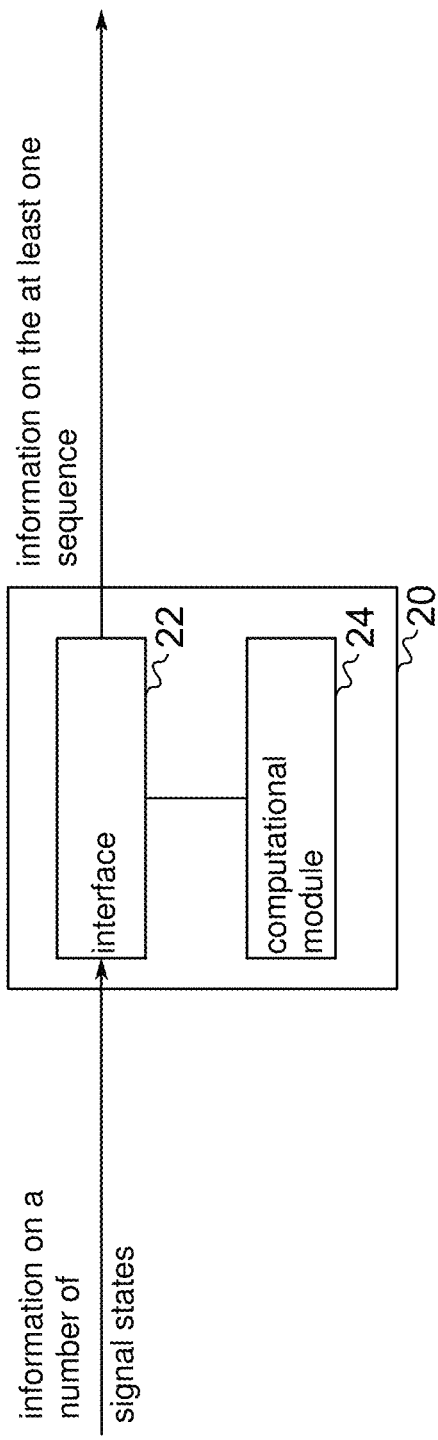
FIG. 1 shows a block diagram of an embodiment of a device for providing information on at least one sequence.

Various embodiments will now be described in more detail with reference to the accompanying drawings in which some example embodiments are illustrated. In the Figures, the thicknesses of lines, layers and/or regions may be exaggerated for clarity.

Like numbers refer to like or similar components throughout the following description of the included Figures which merely show some exemplary embodiments. Moreover, summarizing reference signs will be used for components and objects which occur several times in one embodiment or in one Figure but are described at the same time with respect to one or several features. Components and objects described with like or summarizing reference signs may be implemented alike or also differently, if applicable, with respect to one or more or all the features, e.g. their dimensioning, unless explicitly or implicitly stated otherwise in the description.

Although embodiments may be modified and changed in different ways, embodiments are illustrated as examples in the Figures and are described herein in detail. It is to be noted, however, that it is not intended to restrict embodiments to their respectively disclosed forms but that embodiments ought to cover any functional and/or structural modifications, equivalents and alternatives, which are in the field of the invention. Like reference signs refer to like or similar elements throughout the whole description of the Figures.

It is to be noted that an element designated to be "connected" or "coupled" to another element may be directly connected or coupled to the other element or intervening elements may be present. If an element is designated as "directly connected" or "directly coupled" to another element, there are no intervening elements in between. Different terms which are used to describe the relationship between elements ought to be interpreted likewise (e.g. "between" versus "directly between", "adjacent" versus "directly adjacent" etc.).

The terminology used herein only serves for the description of certain embodiments and should not restrict the embodiments. As used herein, the singular forms such as "a", "an" and "the" should also include the plural forms as long as not clearly indicated otherwise by the context. Further, it is to be clarified that the terms like e.g. "contain", "containing", "comprise", "include", "including" and/or "comprising" as used herein specify the presence of the stated features, integers, steps, operations, elements and/or components but do not preclude the presence or addition of one or more of the features, integers, steps, operations, elements, components and/or any group thereof.

Unless otherwise defined, all terms (including technical and scientific terms) are used herein in their ordinary meaning of the art understood by a person of ordinary skill in the field to which the embodiments belong. It is further to be clarified that terms, e.g. those defined in commonly used dictionaries, should be interpreted as having a meaning that is consistent with their meaning in the context of the relevant art and are not to be described in an idealized or overly formal sense, as far as not expressly defined otherwise herein.

Figure 2:
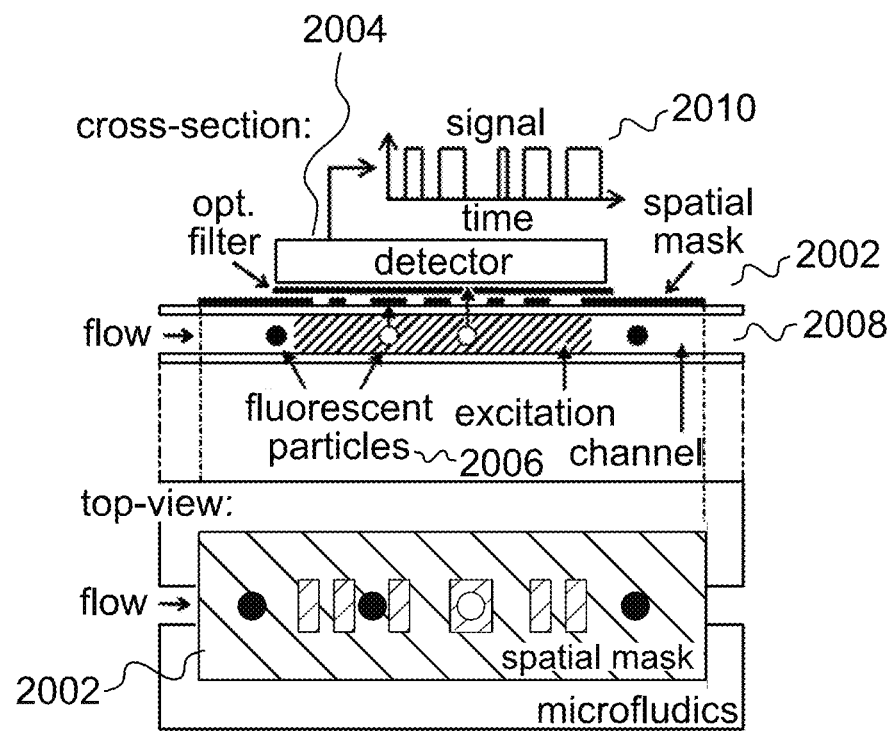
FIG. 2 shows a diagram of the principle of spatially-modulated fluorescence.

In cell counting based on the principle of spatially modulated fluorescence (RMF) frequently binary codes are used using which the spatial modulation sequence of illumination or fluorescence emission is determined (see FIG. 2).

FIG. 2 shows a diagram of a principle of spatially modulated emission. The order of the open and closed areas of the mask 2002 is described by so-called binary sequences/codes, wherein conventionally a "1" in the code is used for mask opening and "0" is used for closed areas. FIG. 2 additionally shows a sensor 2004 which detects a light signal of fluorescent particles 2006 in a channel 2008 and provides the same as a filtered signal 2010.

Figure 3:
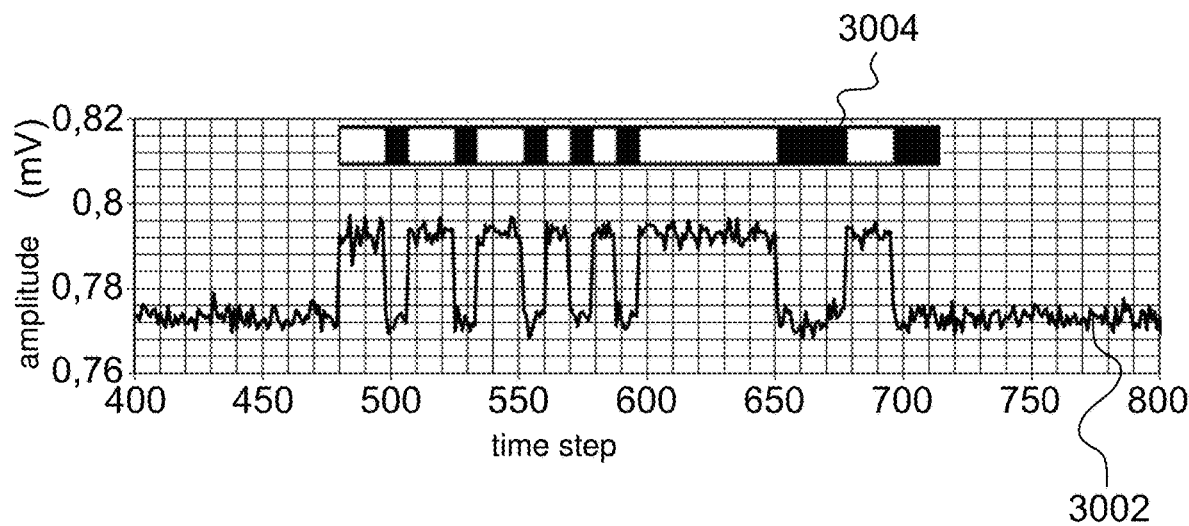
FIG. 3 shows a diagram of a temporal and spatial mapping of a sequence.

In the non-processed output signal 2010 of the RMF, the spatial modulation order may be found again in a corresponding temporal modulation of the signal amplitude (useful signal) (see FIG. 3). Real signals may consist of an additive overlaying of the useful signal, a direct component and noise which may come from different sources (e.g. detector noise, shot noise, quantization noise, etc.). FIG. 3 shows an example for an output signal 3002 encoded with the sequence LABS26(16) (S110110110101011111110001100T). LABS stands for Low-Autocorrelation Binary Sequences, a known group of sequences with low autocorrelation. 3004 shows the corresponding filter.

For determining the transit time and the fluorescence intensity of the cells, in the RMF a continuous correlation 4004 of the input signal with the underlying sequence (filter, 4002) which is extended to the length of the measurement signal (Kiesel et al. 2009) may be executed. The correlation/filtering result 4004 may subsequently be differentiated to suppress 4006 direct components and the low-frequency background component. FIG. 4 shows filter 4002 and correlation signal 4004 including main peak, direct component and low-frequency component. 4006 shows a temporally differentiated correlation signal for eliminating the direct components of the low-frequency component (differential filtering).

In the output signal, apart from a main lobe representing the cell event, significant side lobes may remain which may complicate the detection of the main signature in case of overlapping particles. In embodiments, side lobes may for example correspond to local maxima in a correlation function which are not associated with a main lobe. The local maxima may, for example, be based on an absolute value function and indicate a maximum for a (positive or negative) deviation from a reference value. In some embodiments, a side lobe may also correspond to a side lobe.

FIG. 5 exemplarily shows how by means of a balanced filtering in a correlation step an output signal 5004 with reduced noise amplification may be gained from the input signal of FIG. 3 3002. Using this method, the computational effort may be reduced and/or the signal-to-noise ratio (SNR) may be improved. However, side lobes with a comparable amplitude may remain in the signal. FIG. 5 shows a balanced filter 5002 for the sequence LABS26 and an output signal 5004 with a main lobe and side lobes. 5006 shows the absolute amount of the output signal. As compared to FIG. 4, the direct component is directly eliminated and the low-frequency component is clearly reduced. As compared to 4006, the output signal is clearly less noisy, side lobes with a comparable amplitude may remain in the signal, however.

Figure 6:
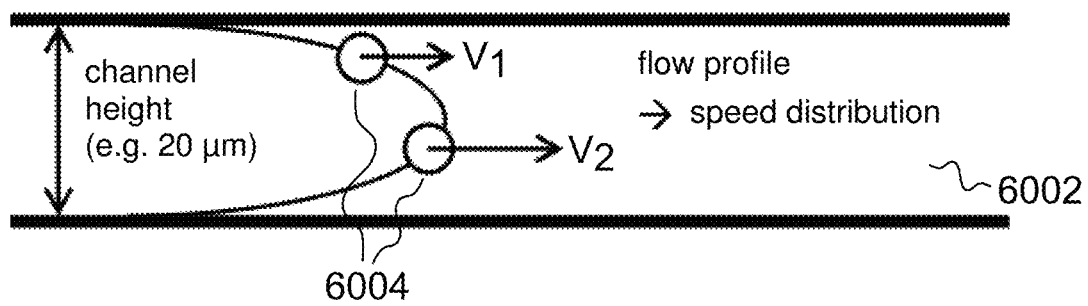
FIG. 6 shows a lateral transport speed of cells in a fluidic flow profile in a channel.

The temporal extent of the signal is frequently unknown, as e.g. in case of a microfluidic cell count the lateral transport speed of cells 6004 depends on their transport position in the fluidic flow profile 6002 (see FIG. 6). To still be able to identify cells, now the correlation of the signal may take place with a plurality of filters so that the complete expected speed/run time range of the object is covered. The filtering may, for example, take place on a plurality of so-called speed channels 7002 (see FIG. 7) and is also called two-dimensional (2D) correlation.

Figure 7:
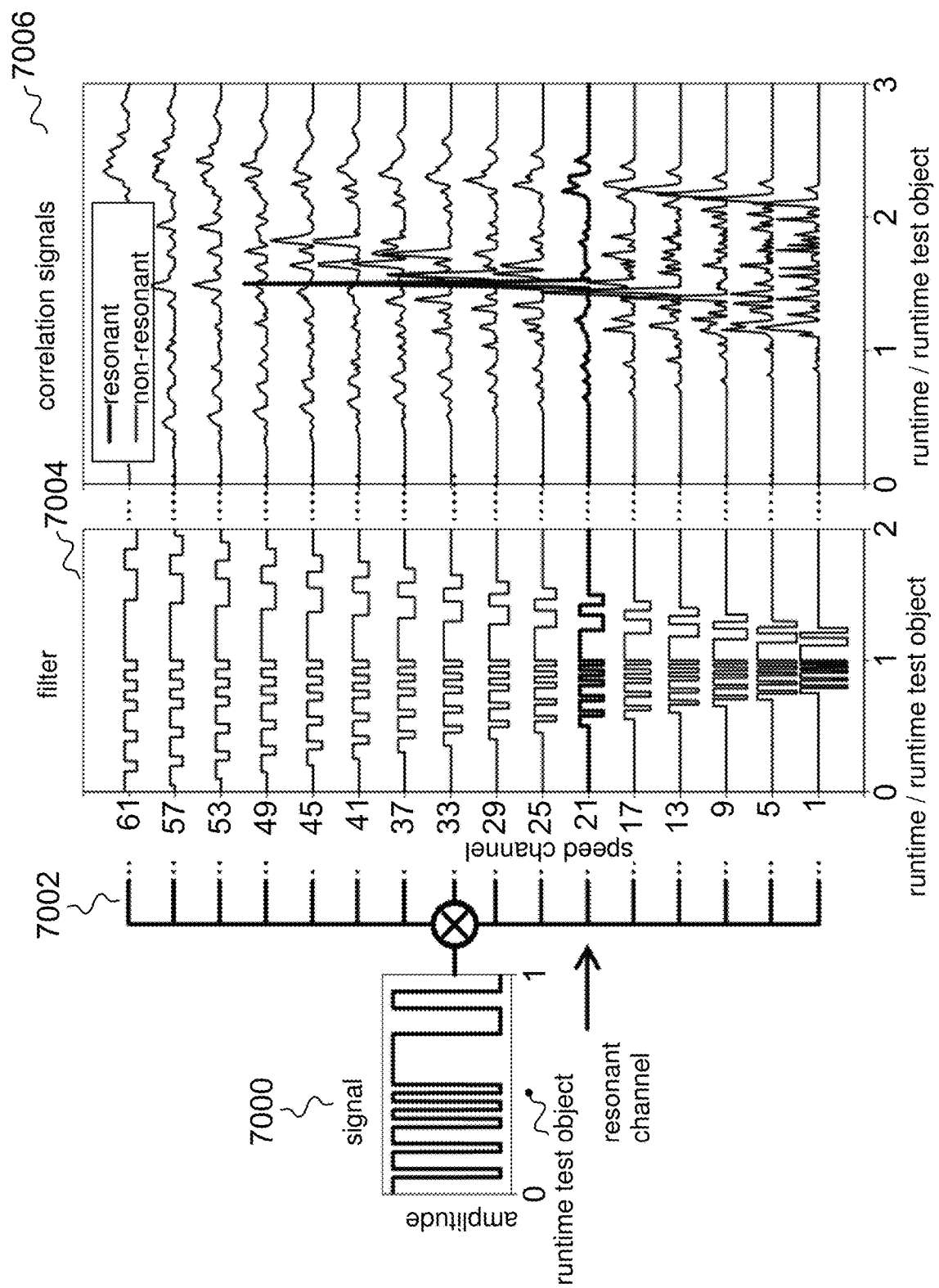
FIG. 7 shows a balanced filtering of an input signal comprising a plurality of filters.

FIG. 7 shows a balanced filtering of an input signal 7000 with a plurality of filters 7004 on the speed channels 7002. The filters 7004 are temporally stretched to detect the actual length of the input signal 7000. Additionally, the amplitudes of the filters are normalized in order to reproduce the amplitude of the input signal on the output side. From the global maximum across all correlation/output signals 7006 the input signal amplitude, the transport speed of the object and the time of transit result.

In the output signals, for example, from the global maximum (greatest main lobe) a so-called resonant speed channel may be determined. In at least some embodiments, a speed channel or also channel may correspond to a temporally-scaled sequence or a filter based on a temporally-scaled sequence. In this channel, the length of the input signal corresponds to the length of the filter and, for example, the signal amplitude, the speed and the time of the cell transit may be determined. However, the non-resonant channels may show distinct maxima which are clearly higher regarding the amplitude than the side lobes on the resonant channel. In the 2D correlation, when using the known LABS on the non-resonant channels, distinct side lobes may occur. This has three main consequences:

Noise in the input signal may cause the side lobes to be increased clearly above their regular level so that erroneous detections occur. Threshold values for the event detection may be sufficiently high in order to prevent erroneous detections. The detection limit is consequently given by the amplitude of the greatest side lobes.

In case of overlapping input signals, i.e. with a simultaneous transit of several cells through the detection zone, the amplitudes of the main lobes may be strongly corrupted by the side lobes of the neighboring events or due to constructive overlaying of side lobes erroneous detections may result.

In case of overlapping cell signals the amplitude of the weaker signal may still be clearly lower than the greatest side lobes of the stronger signal. The measurement range dynamics may be strongly limited in the time range around the main lobe in which the side lobes are located.

Embodiments are based on the finding that it may be sensible to minimize the maximum amplitude of the side lobes for the case of different cell speeds—i.e. for the 2D case—also on the non-resonant speed channels. At least some embodiments describe according to which criteria codes are to be selected which fulfill this requirement.

FIG. 1 shows a block diagram of an embodiment of a device 20 for providing information on at least one sequence. The at least one sequence describes temporally successive signal states. A signal state might correspond to a binary, a unipolar, a bipolar or a multipolar signal state. A signal state may include a logical or discrete value or be based on a voltage, a current strength and/or a measuring intensity. In at least some embodiments, the sequence may describe temporally equidistant signal states or the sequence may describe a variable temporal connection between signal states. In at least some embodiments, a sequence may correspond to a binary sequence. The binary sequence may, for example, describe temporally equidistant successive signal states.

The device 20 includes an interface 22 which is implemented to receive information on a number of the signal states. The interface 22 may, for example, correspond to one or several inputs and/or one or several outputs for receiving and/or transmitting information, e.g. in digital bit values, based on a code, within a module, between modules or between modules of different entities. The information on the number of the signal states may, for example, include information on a number of time steps in the sequence, information on a number of signal state changes and/or information on a length of the sequence.

The device 20 further includes a computational module 24 which is implemented to generate a plurality of possible sequences based on the information on the number of the signal states. In some embodiments, the plurality of the possible sequences may include all sequences which are possible based on the number of the signal states and based on the signal states. With binary signal states and a number of 5 signal states the plurality of possible sequences may, for example, include 32 sequences. In at least some other embodiments the plurality of possible sequences may include a subset of possible sequences which is for example restricted by characteristics of the sequences, for example by a periodicity or an average structural length.

In embodiments, the computational module 24 may correspond to any controller or processor or a programmable hardware component. For example, the computational module 24 may also be realized as software which is programmed for a corresponding hardware component. In so far, the computational module 24 may be implemented as a programmable hardware with correspondingly adapted software. Here, any processors, like digital signal processors (DSPs) may be used. Embodiments are here not restricted to a certain type of processor. Any processors or also several processors are possible for implementing the computational module 24.

In at least some embodiments, a sequence may have an average structural size. A structural size may be based on a number of equal successive signal states. The computational module 24 may be implemented to generate the plurality of possible sequences based on a target area for the average structural size.

The average structural size may correspond to an average of the structural sizes of a sequence. In at least some embodiments, the target area for the average structural size may lie between 1.3 and 1.8. In some embodiments, the target area may, for example, lie between 1.4 and 1.7, between 1.5 and 1.6, between 1.4 and 1.7, between 1.5 and 1.7 or between 1.4 and 1.6.

The computational module 24 is further implemented to calculate correlation functions between a sequence and at least a temporal scaling of the sequence for at least one subset of the possible sequences. A correlation function includes a main lobe and one or several side lobes.

The at least one temporal scaling of the sequence may, for example, be based on differently long temporal extensions of the signal states. In at least some embodiments, the at least one temporal scaling of the sequence may be based on a mapping of the sequence to different numbers of sampling times or comparison times. For example, the at least one temporal scaling of the sequence may include temporally-scaled sequences having 2 sampling times or comparison times (samples) per state change, 3 samples per state change, 4 samples per state change, etc.

The correlation functions may, for example, correspond to cross-correlation functions. The sequence may, for example, be based on a temporal reference scaling and the computational module 24 may be implemented to calculate the cross-correlation functions between the temporal reference scaling of the sequence and the at least one temporal scaling of the sequence. In at least some embodiments, the correlation functions may include autocorrelation functions. In some embodiments, the computational module 24 may further be implemented to calculate the autocorrelation function of the sequence based on the temporal reference scaling and/or autocorrelation functions of the temporally-scaled sequences. In some embodiments in which the at least one temporal scaling of the sequence includes two or more different temporal scalings of the sequence, the computational module 24 may further be implemented to calculate cross-correlation functions between different temporally-scaled sequences of the two or more different temporal scalings of the sequence.

The computational module 24 may be implemented to determine the subset of the possible sequences based on the average structural size. Alternatively or additionally, the computational module 24 may be implemented to determine the subset of the possible sequences based on the target area for the average structural size.

The computational module 24 is further implemented to determine the at least one sequence based on the correlation functions. The series of signal states within the at least one sequence is selected such that a side lobe in a correlation function of the sequence comprising the at least one temporal scaling of the sequence is reduced as compared to a side lobe which may maximally be acquired in a correlation function by different arrangements of the signal states in the sequence.

The computational module 24 is further implemented to determine the information on the at least one sequence based on the at least one sequence and provide the same via the interface 22. The interface 22 is coupled to the computational module 24.

In at least some embodiments the computational module 24 may be implemented to determine the plurality of possible sequences as unipolar sequences. In some embodiments, the computational module 24 may further be implemented to calculate the correlation functions based on the unipolar sequences and/or to determine the at least one sequence based on the unipolar sequences. In at least some embodiments, the computational module 24 may further be implemented to determine the temporally-scaled sequences as balanced temporally-scaled sequences, to determine the temporally-scaled sequences as normalized temporally-scaled sequences and/or to calculate the correlation functions based on the balanced temporally-scaled sequences and/or the normalized balanced temporally-scaled sequences.

In some embodiments, the computational module 24 may be implemented to determine the at least one sequence based on the correlation functions. The sequence of the signal states within the at least one sequence may be selected such that a sum which is based on the side lobes of a correlation function of the sequence comprising the at least one temporal scaling of the sequence is reduced as compared to a sum which may maximally be acquired by different arrangements of the signals based on the sequence, wherein the sum is based on the side lobes resulting from the different arrangement. The sums may for example be based on numerical representations of the correlation functions. The sums may, for example, be based on squaring or amount functions of the numerical representations of the side lobes, for example divided by the number of considered time steps. The sums may, for example, be normalized.

Alternatively or additionally, the sequence of signal states within the at least one sequence may be selected such that a greatest side lobe in the correlation function of the sequence comprising the at least one temporal scaling of the sequence is reduced as compared to a greatest side lobe which may maximally be acquired by different arrangements of the signal states in the sequence. The greatest side lobe may, for example, be based on a squaring or amount function of the numerical representation of the side lobes.

In some embodiments, the computational module 24 may be implemented to determine the at least one sequence so that the sum which is based on the side lobes is below a first threshold value.

The first threshold value may, for example, correspond to a second-lowest sum which is based on the side lobes of the correlation functions. The computational module 24 may recursively calculate the second-lowest sum. For example, the computational module 24 may iteratively calculate the correlation functions, wherein the computational module 24 uses the sum which is lowest at that time which is based on the side lobes of the correlation function as the first threshold value.

In at least some embodiments, the first threshold value may be based on a lowest sum which is based on side lobes of correlation functions between sequences and temporally-scaled sequences based on at least one element of the group of low autocorrelation binary sequences (LABS), Barker-codes, CS100 codes, S100 codes, Neuman-Hofman codes, Merten's codes.

The computational module 24 may be implemented to determine the at least one sequence so that the greatest side lobe is below a second threshold value. The second threshold value may correspond to a greatest side lobe of a sequence comprising a second-lowest greatest side lobe of the correlation functions. The computational module 24 may calculate the second-lowest greatest side lobe iteratively or recursively, for example. For example, the computational module 24 may iteratively calculate the correlation function, wherein the computational module 24 uses the side lobe which is lowest at this time which is based on the side lobes of the correlation functions as the second threshold value. In at least some embodiments, the one or several side lobes and/or the main lobe may be normalized.

In some embodiments, a lowest greatest side lobe may correspond to a side lobe which, in a plurality of correlation functions between sequences and temporally-scaled sequences of a plurality of different sequences, wherein the correlation functions each include a greatest side lobe, represents the lowest greatest side lobe.

In some embodiments, the first threshold value may be based on a lowest greatest side lobe of correlation functions between sequences and temporally-scaled sequences based on at least one element of the group of low autocorrelation binary sequences (LABS), Barker-codes, CS100 codes, S100 codes, Neuman-Hofman codes, Merten's codes.

In conventional systems also for unipolar signals so-called "low autocorrelation binary sequences" (LABS) are used for the definition of the signal component. These sequences are bipolar, i.e. the coefficients are either "1" or "−1" and may, for example, be optimized for bipolar and DC-free signals. Optimizing may for example be intended to either minimize the overall energy (or amplitude) in the side lobes or the energy/amplitude of the greatest side lobe. The already above introduced sequence LABS26 is such a sequence with the length 26. In the conversion of a bipolar (1,−1) sequence into a unipolar (0,1) sequence, the following two transformation regulations are used:

$$-1 \rightarrow 40, 1 \rightarrow 1 \qquad (1)$$

$$-1 \rightarrow 1, 1 \rightarrow 0 \qquad (2)$$

i.e., from one bipolar sequence two unipolar sequences may be generated which may behave differently within the sense of the characteristics described in the following. In the following both sequences were examined each.

In FIG. 8, for the sequence LABS26, the bipolar, DC-free signal 8002, the filter component 8004 and the output signal 8006 are represented. It is obvious as compared to FIG. 4 that the main lobe ($A_H$) is substantially greater than the highest side lobe (max(abs($NK_i$))), ($NK_i$ designates the i-th side lobe). In this case, for the bipolar situation the following ratio results $$V_{bip} = \frac{A_H}{\max(\text{abs}(NK_i))} 77, 4 \qquad (3)$$

For the two unipolar cases $V_{differentiell}$=15,1 and $V_{balancier}$=13,0 result.

In case of RMF the form of the signals is now unipolar and with DC, as illustrated by the example signal 3002 of FIG. 3. At least some embodiments illustrate that in case of such unipolar signals a new class of sequences may be advantageous which is different from the already known LABS. Using an exemplary sequence (Q1DP26(12,#1) [01001001010111011000111000]) FIG. 2 illustrates that a substantially improved main lobe to side lobes ratio V may be acquired as compared to prior bipolar LABS (Levanon et al. 2004, Turyn et al. 1961, Mertens et al. 1996, Coxson et al., 2005, Borewein et al. 2000, Nunn et al. 2008, Shanmugam et al. 2008). Thus, for example, for the code length 26 an improved ratio found in embodiments using the sequence Q1DP26(12,#1) is $V_{bal}$(Q1DP26(12, #1))=46.0. For prior LABS the best-found ratio is $V_{bal}$(LABS26)=13.0. In embodiments, a code may correspond to a sequence.

FIG. 9 shows the unipolar signal 9002 with DC component, the filter component 9004 and the output signal 9006 for a sequence Q1DP26(12,#1) of embodiments.

In the following, as an example, an evaluation model for the sequence/code quality for the case of a known signal length (1D and/or one-dimensional case) is defined. A unipolar sequence (code) C having the length L is defined by L coefficients $b_i$:

$$C=[b_i], (i=1,2,\ldots,L), b_i \in \{1,0\} \qquad (4)$$

The number E of ones in the code is then calculated according to $$E = \sum_{i=1}^{L} b_i \qquad (5)$$

and the number Z of zeros in the code is $$Z = L - E \qquad (6)$$

A section $M_j$ of the length $K_M$ of the measurement signal for the time steps $t_j, t_{j+1}, \ldots, t_{j+K_M-1}$ is defined by a sequence of $K_M$ temporally equidistant values $m_{j+k-1}$, (k=1, 2, ..., $K_M$) which are each additively put together from a quasi-stationary DC component $g_{j+k-1}$=g, a noise component $r_{j+k-1}$ and the actual useful signal S with the individual values $a_{j+k-1}$, which take on the useful signal amplitude A if: $b_i$=1 applies in the time step $t_{j+k-1}$. I.e., at the time $t_{j+k-1}$, the fluorescent particle 2006 is located in a place relative to the mask 2002, where the detector or sensor 2004 "sees" the signal of the particle (see FIG. 2). Otherwise, $a_{j+k-1}$=0 applies. Consequently, the following results:

$$M_j=[m_{j+k-1}]=[a_{j+k-1}+G+r_{j+k-1}],$$

$$(j=1,2,\ldots),(k=1,2,\ldots,K_M), a_{j+k-1} \in \{A,0\} \qquad (7)$$

The overall length $K_v$ of the useful signal S in the measurement signal $M_j$ is calculated from the average number of time steps $K_{bv}$ during which the particle is located in the area of a code coefficient $b_i$ and from the code length L $$K_v = K_{bv} L \qquad (8)$$

In at least some embodiments, $K_{bv}$ need not be an integer. For a simplification, the following considerations are only executed for integer values of $K_{bv}$.

The filter $F_v$ with the coefficients $f_{k \cdot i,v}$ is to be selected having the length $K_v$ of the useful signal to guarantee an improved detection and its coefficients are occupied according to the following regulation. For each code coefficient $b_i$ $K_{bv}$ filter coefficients $f_{k \cdot i,v}$ may be selected so that the following applies:

$$f_{k \cdot i,v} = f_{p,v} = \begin{cases} h = \dfrac{1}{EK_{bv}}, & \text{falls } b_i = 1 \\ l = -\dfrac{1}{ZK_{bv}}, & \text{falls } b_i = 0 \end{cases}, \quad (9)$$

$$(p = k \cdot i = 1, 2, \ldots, K_v)$$

Based on this selection, the filter $F_v$ in embodiments may be balanced, i.e. the following applies $$\sum_p f_{p,v} = 0, \ (p = 1, 2, \ldots, K_v) \tag{10}$$

and the filter $F_v$ may be normalized so that the main lobe after the correlation takes on the value A of the useful signal amplitude in the useful signal S (noise-free case). If a useful signal with the amplitude A is comprised in the measurement signal section $M_j$, for the (noise-free) correlation signal C the following may apply $$\max(c_q)_{j,v} = \max\left(\sum_{p=1}^{K_v} m_{j+q-1+p-1} f_{p,v}\right) = A, \tag{11}$$

$$(q = 1, 2, \ldots, K_M - K_v + 1)$$

Generally, here the coefficients of the correlation $C_{j,v} = M_j \times F_v = [c_{q,j,v}]$ of the measurement signal $M_j$ of the length $K_M$ with the filter $F_v$ are defined as follows:

$$c_{q,j,v} = \sum_{p=1}^{K_v} m_{j+q-1+p-1} f_{p,v}, \ (q = 1, 2, \ldots, K_M - K_v + 1) \tag{12}$$

So that in the correlation all coefficients are completely included, i.e. also all side lobes, the measurement signal may at least comprise a length $K_M = 3K_v - 2$.

For characterizing different codes, in embodiments the measurement signal may now be simplified by setting the DC component $g=0$ and by neglecting the noise ($r_{j+k-1} = 0 \forall k$), i.e. the code characterization may be executed only using the useful signal. For a further simplification, the amplitude of the useful signal is set to $A=1$ in order to receive a simplified filter test signal. The filter test signal $S_{T,v}$ for an object of the speed v may then have the following form:

$$S_{T,v} = [s_{p,v}], \tag{13}$$

wobei $s_{p,v} = s_{k \cdot i,v} = \begin{cases} 1, & \text{falls } b_i = 1 \\ 0, & \text{falls } b_i = 0 \end{cases}, (p = 1, 2, \ldots, K_v)$ As under these circumstances in embodiments coefficients outside the filter test signal and the filter may be assumed to be zero, the correlation of both signals may be represented as follows:

$$c_{q,v} = \sum_{p=1}^{K_v} s_{p,v} f_{p+q-K_v}, \ (q = 1, 2, \ldots, 2K_v - 1), \tag{14}$$

wobei $s_{x,v} = f_x = 0$, für $x < 1$ oder $x > K_v$

The correlation for example has $2K_v - 1$ correlation coefficients. Of those, per definition the coefficients having the index $K_v - (K_{bv} - 1)$, $K_v - (K_{bv} - 1) + 1$, ..., $K_v + (K_{bv} - 1)$, i.e. overall $(2K_{bv} + 1)$ coefficients are associated to the main lobe and all other coefficients belong to the side lobes. This definition suggests that the main lobe contains double as many correlation coefficients as there are time steps in a code coefficient. In order to be able to treat positive and negative values alike, the correlation coefficients in at least some embodiments may be squared and the maximum $$1DPSLR = \max(c_{q,v}^2)$$

$$\text{für } q \neq K_v - (K_{bv} - 1), K_v - (K_{bv} - 1) + 1, \ldots, K_v + (K_{bv} - 1) \tag{15}$$

may indicate a characteristic value for the greatest side lobe of the code, wherein all correlation coefficients in an overall width of $(2K_{bv} + 1)$ around the main lobe are excluded. In at least some embodiments, the greatest side lobe may be based on 1DPSLR.

An average value $$1DISLR = \frac{\Sigma_q c_{q,v}^2}{2K_v - 1 - 2(K_{bv} - 1)} \tag{16}$$

$$\text{für } q \neq K_v - (K_{bv} - 1),$$
$$K_v - (K_{bv} - 1) + 1, \ldots, K_v + (K_{bv} - 1)$$

is, for example, a further characteristic value for the energy/amplitude contained in the side lobes, wherein also all correlation coefficients of an overall width of $(2K_{bv+1})$ around the main lobe are omitted. In at least some embodiments, the sum of the side lobes may be based on 1DISLR.

Alternatively, as a range for the main lobe, all correlation coefficients up to the two neighboring local minima may be used.

A further parameter for the assessment of sequences regarding their suitability for the RMS technology is noise amplification in some embodiments. Generally, noise gain V may be calculated as follows $$V_v = \sqrt{\sum_{p=1}^{K_v} f_{p,v}^2} \tag{17}$$

From the ratio of input signal amplitude (=amplitude of the main lobe with balanced codes) to noise gain the SNR gain for example results $$SNR_{Gain,v} = \frac{A}{\sqrt{\sum_{p=1}^{K_v} f_{p,v}^2}} = \frac{1}{\frac{1}{A}\sqrt{\sum_{p=1}^{K_v} f_p^2}} = \sqrt{K_b}\sqrt{\frac{E \cdot Z}{L}} \quad (18)$$

The SNR gain of a balanced filter in connection with unipolar modulation sequences may occupy a maximum for E=Z for an even L or abs(E−Z)=1 for an odd L.

A code may fulfill two conditions:
1. It has an improved $SNR_{Gain}$ and
2. it has a decreased 1DISLR or 1DPSLR Mathematically, this may e.g. be summarized in the quality index numbers $$Q1DI = \frac{SNR_{Gain}}{1DISLR} \quad (19)$$

and $$Q1DP = \frac{SNR_{Gain}}{1DPSLR} \quad (20)$$

In at least some embodiments, the greatest side lobe may be based on Q1DP. In at least some embodiments, the sum of the side lobes may be based on Q1DI.

Figure 10:
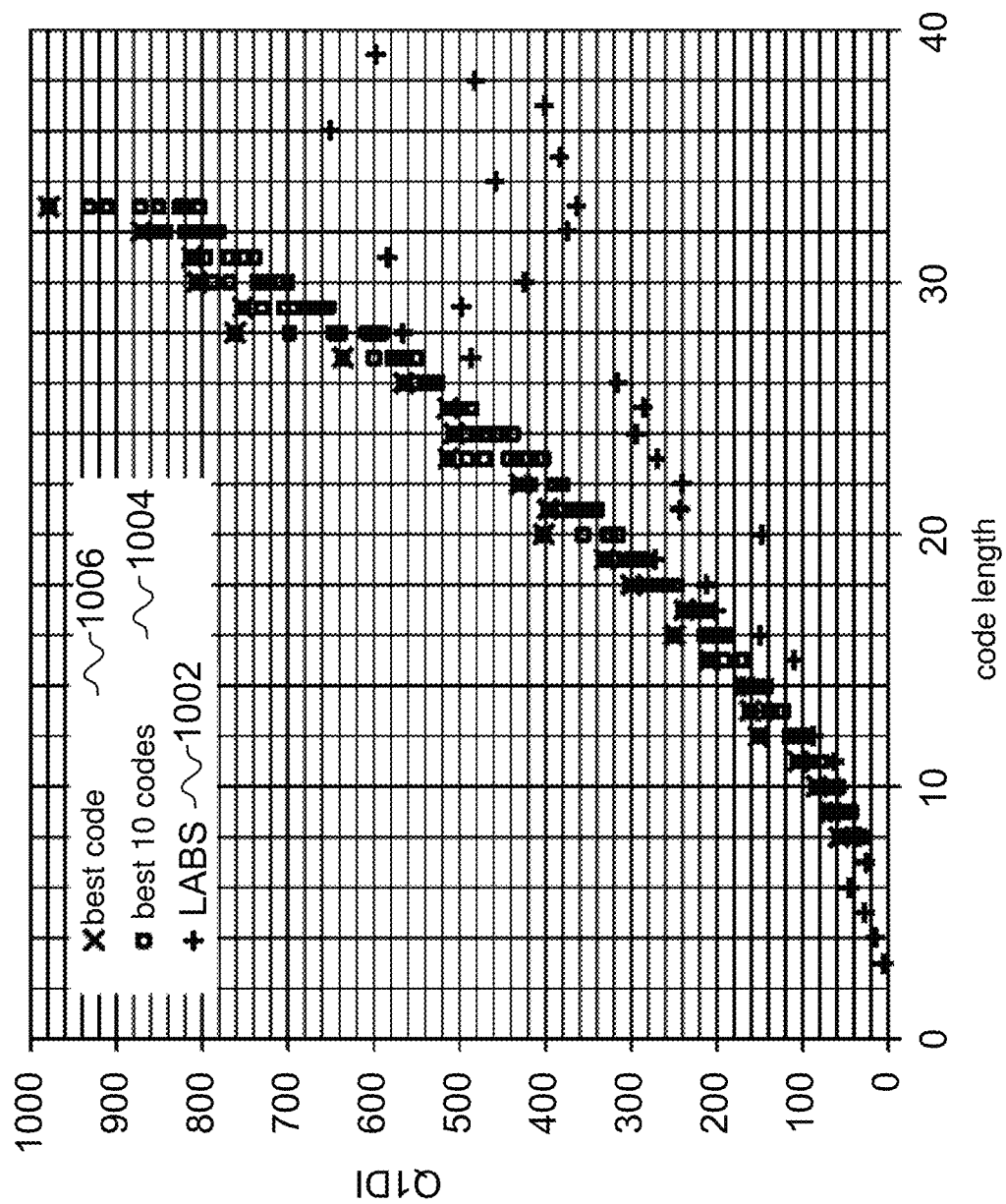
FIG. 10 shows a comparison of the quality index number Q1D1 for sequences from a class of LABS and ULABS.
Figure 12:
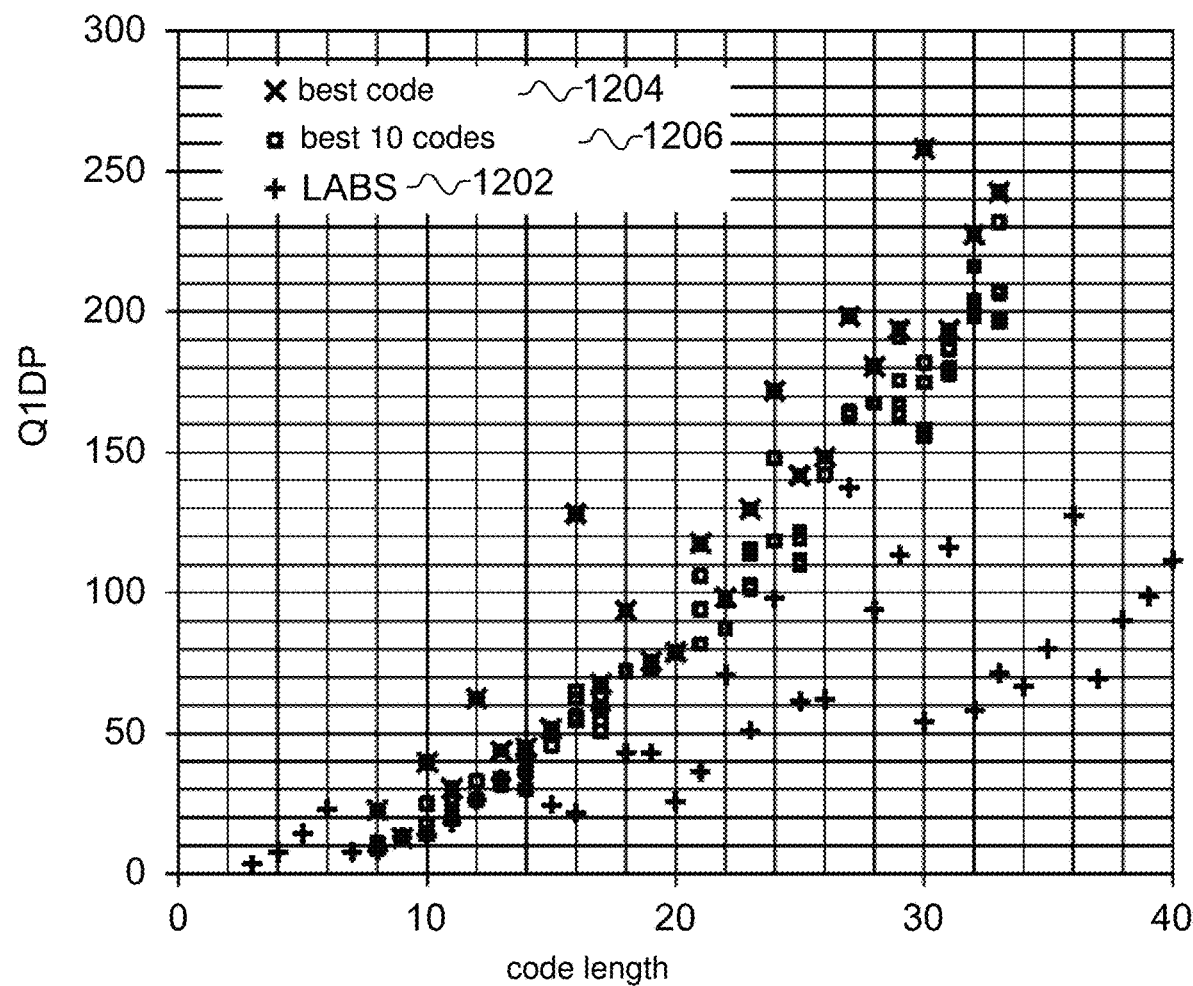
FIG. 12 shows a comparison of a quality index number Q1DP for sequences of a class of LABS and ULABS.

In exemplary embodiments, a complete search in all codes up to a length L=33 indicated that numerous unipolar codes "ULABS" exist which using those criteria may be better suitable for being used in RMF (and comparable applications which use unipolar codes) than the known bipolar LABS (see FIG. 10 and FIG. 12, the associated codes and quality index numbers may be found in FIG. 11 and FIG. 13).

In at least some embodiments, the terms best codes, optimum codes, best sequences or optimum sequences refer to sequences which, when considering one or several criteria or quality index numbers, like Q1D1,Q1DP, Q2DI, Q2DP, Q2DPs, comprise advantageous or the most advantageous characteristics among a plurality of considered sequences.

FIG. 10 shows a comparison of the quality index number Q1DI for the known LABS (best LABS 1002) and examples from the class of codes "ULABS" of embodiments (best code: 1004, best 10: 1006).

In an exemplary embodiment, FIG. 11 each shows the best considered sequences from the class of LABS 1116 and the ULABS 1114 evaluated according to the quality index number Q1DI 1112. 1102 shows a code ID of the codes, 1104 a binary representation of the codes, 1106 the code length, 1108 the number of ones in the binary code, 1110 shows $SNR_{Gain}$ and 1112 the quality index number Q1DI.

FIG. 12 exemplarily shows a comparison of the quality index number Q1DP for the known LABS (best LABS: 1202) and examples from the newly-identified class of codes "ULABS" (best code: 1204, best 10: 1206).

In one exemplary embodiment FIG. 13 shows each the best considered sequences from the class of LABS 1316 and the ULABS 1314 evaluated according to the quality index number Q1DP 1312. 1302 shows the code ID of the code, 1304 a binary representation of the sequences, 1306 the sequence length, 1308 the number of ones in the binary sequence, 1310 shows $SNR_{Gain}$ and 1312 the quality index number Q1DP.

Figure 14:
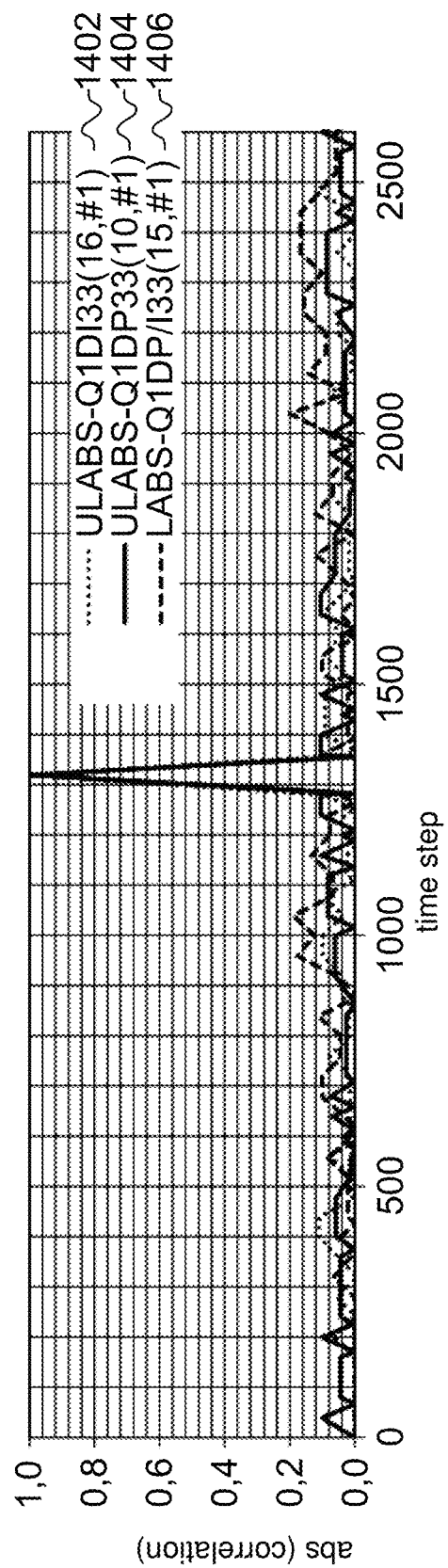
FIG. 14 shows a comparison of the respectively best examined sequences of the embodiments with L=33 with respect to the quality index numbers Q1DP and Q1DI.

FIG. 14 shows a comparison of the best sequences each 1402 (Q1DI) and 1404 (Q1DP) from the embodiments with L=33 of FIG. 11 and FIG. 13 with respect to the quality index numbers Q1DP 1312 and Q1DI 1112. For both criteria, the same LABS 1406 is found.

The hitherto executed calculations and selection criteria relate to the 1D case, i.e. the temporal extent of the input signal and/or the speed of the cell/the object is known. In the following, the criteria are extended to the 2D case. It is already indicated in FIG. 7 that in this case correlating may be executed across a plurality of so-called speed channels, i.e. for each speed an especially adapted filter may be used, for example by different temporal scalings of the sequence. A corresponding filter bank with a set of filters $F_j$ for $K_v$ speed channels may be calculated in embodiments using equation (9).

$$F_j = [f_{(k \cdot i j)}], (i=1,2, \ldots ,L), (k=1,2, \ldots ,K_{bj}), (K_{bj}=K_u, K_u+1, \ldots ,K_o), \quad (21)$$

wherein $K_u \cdot L$ and $K_o \cdot L$ describe the length of the filter for the highest and/or lowest speed in the filter bank.

Analog to equation (13), a test signal $S_T = [s_p]$ comprising $K_T$ ($K_u \leq K_T \leq K_o$) samples per code coefficient is selected and the 2D correlation results analogue to equation (14)

$$c_{qj} = \sum_{p=1}^{K_j} s_p f_{p+q-K_j}, \quad (22)$$

$(q = 1, 2, \ldots , 2K_j - 1), (K_j = L \cdot K_{bj})$ wobei $s_x = f_x = 0$, für $x < 1$ oder $x > K_j$ FIG. 7 shows the form of filters 7004 and correlation signals 7006 (output signals) for selected speed channels 7002. It is found that at least in some embodiments in the so-called resonant channel the greatest main lobe is to be found. Using the parameters $K_u$ and $K_o$ in embodiments now a speed range may be determined in which the side lobes around the main lobe may be assessed. In FIG. 7 $K_u$=20 (channel no. 1, $v_{max,opt}$) and $K_o$=80 (channel no. 61, $v_{min,opt}$) were selected and the resonant channel was set to $K_T$=40 (channel no. 21, $v_{center}$). The shortest filter in one exemplary implementation is set to double the speed of the test particle and the longest filter accordingly to half and the following applies:

$$v_{max,opt}/2 = v_{center} = 2 \cdot v_{min,opt} \quad (23)$$

This relation indicates in what speed range around the main lobe side lobes may exemplarily be examined and minimized. For the application of technology in case of an unknown speed this means that the code is designed with respect to speed dynamics $$[v_{min}; v_{max} = 2 \cdot v_{min}] \quad (24)$$

as this is exactly the speed range in which for the fastest object optimization up to the slowest speed is laid out and vice-versa.

In some embodiments, the computational module 24 may be implemented to determine cleaned-up correlation functions based on the correlation functions. The computational module 24 may be implemented to reduce a contribution of main lobes in the cleaned-up correlation functions. The computation module 24 may, for example, be implemented to determine the information on the at least one sequence based on the cleaned-up correlation functions.

In at least some embodiments, the computational module 24 may be implemented to determine a greatest main lobe among the main lobes of the correlation functions. The computational module 24 may be implemented to reduce the contribution of the main lobes in the cleaned-up correlation function across the temporal extent of the greatest main lobe. For example, the computational module 24 may be implemented to suppress or reduce any other main or side lobes during the temporal extent of the greatest main lobe.

Alternatively or additionally, the computational module 24 may be implemented to determine and to reduce the contributions of the main lobes in the cleaned-up correlation functions of the temporally-scaled sequence and neighboring temporal scalings of the sequence based on a temporal position of the greatest main lobe and based on the correlation function of the temporally-scaled sequence comprising the greatest main lobe. The temporally-scaled sequence which includes the greatest main lobe may for example correspond to a resonant channel. In embodiments, the computational module 24 may be implemented to reduce the contributions of the main lobes up to a next (local) minimum, for example based on the temporal position of the greatest main lobe.

Figure 15:
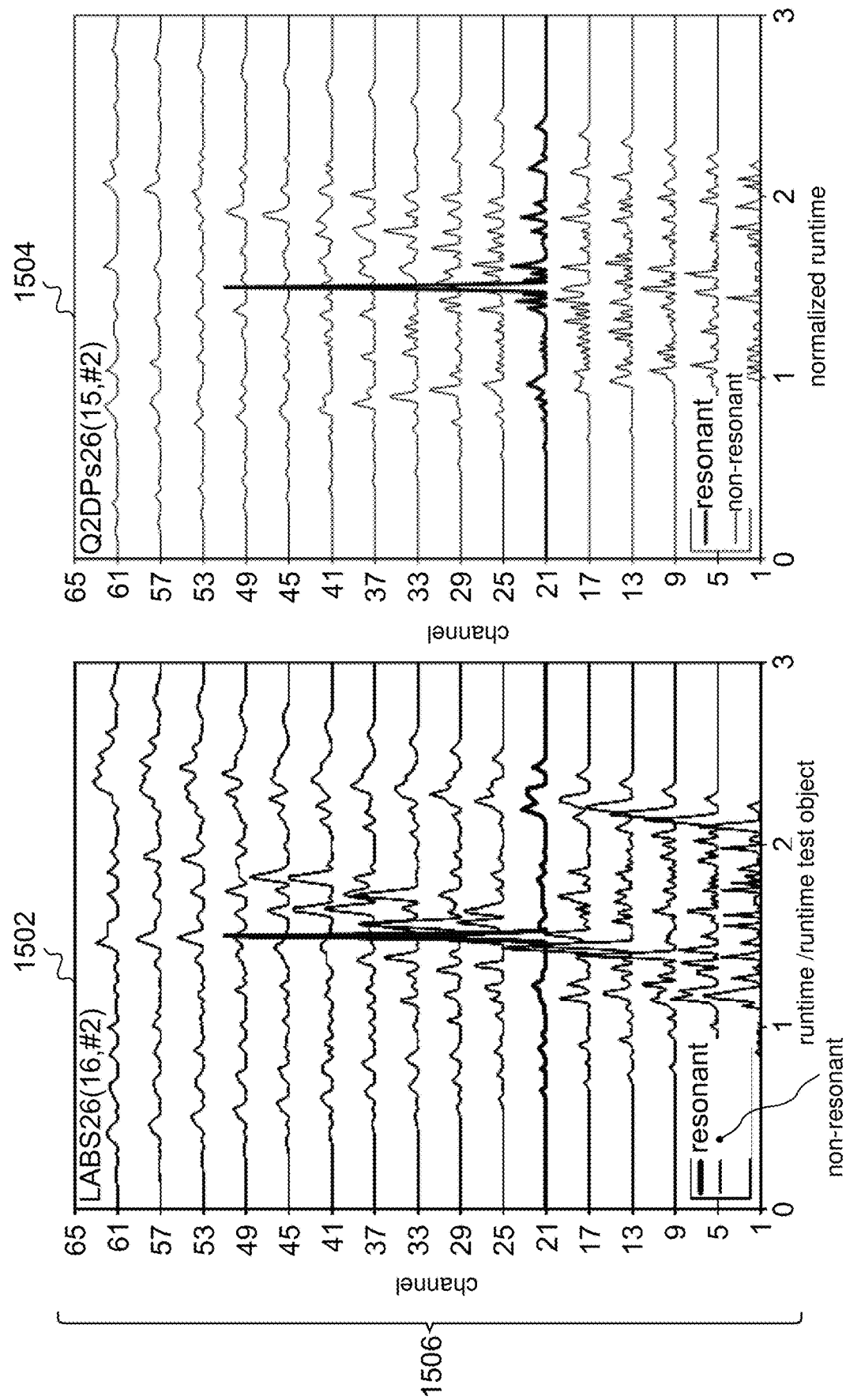
FIG. 15 shows a comparison of 2D squared correlation channels for selected speed channels for LABS26(16,#2) and Q2DPs26(15,#2)

FIG. 15 shows a comparison of 2D squared correlation channels 1506 for selected speed channels for LABS26(16,#2) 1502 and Q2DPs26(15,#2) 1504. Q2DPs26(15,#2) 1504 shows clearly lower side lobes across the complete speed range. For determining quality index numbers for the codes, two differently sharp criteria may be used.

Criterion 1: Cutting out the time range covered by the greatest main lobe on all channels (temporal scalings). Advantage: This criterion may be easy to implement numerically. Disadvantage: Optimizing possibly does not include the case of double events in which one particle overtakes the other exactly in the mask center.

Criterion 2: Cutting out the greatest main lobe in the resonant channel and the main lobes in the neighboring channels (temporal scalings), each up to the next minimum. This criterion may be sharper but numerically more extensive. For overtaking events optimizing may also apply.

Figure 16A:
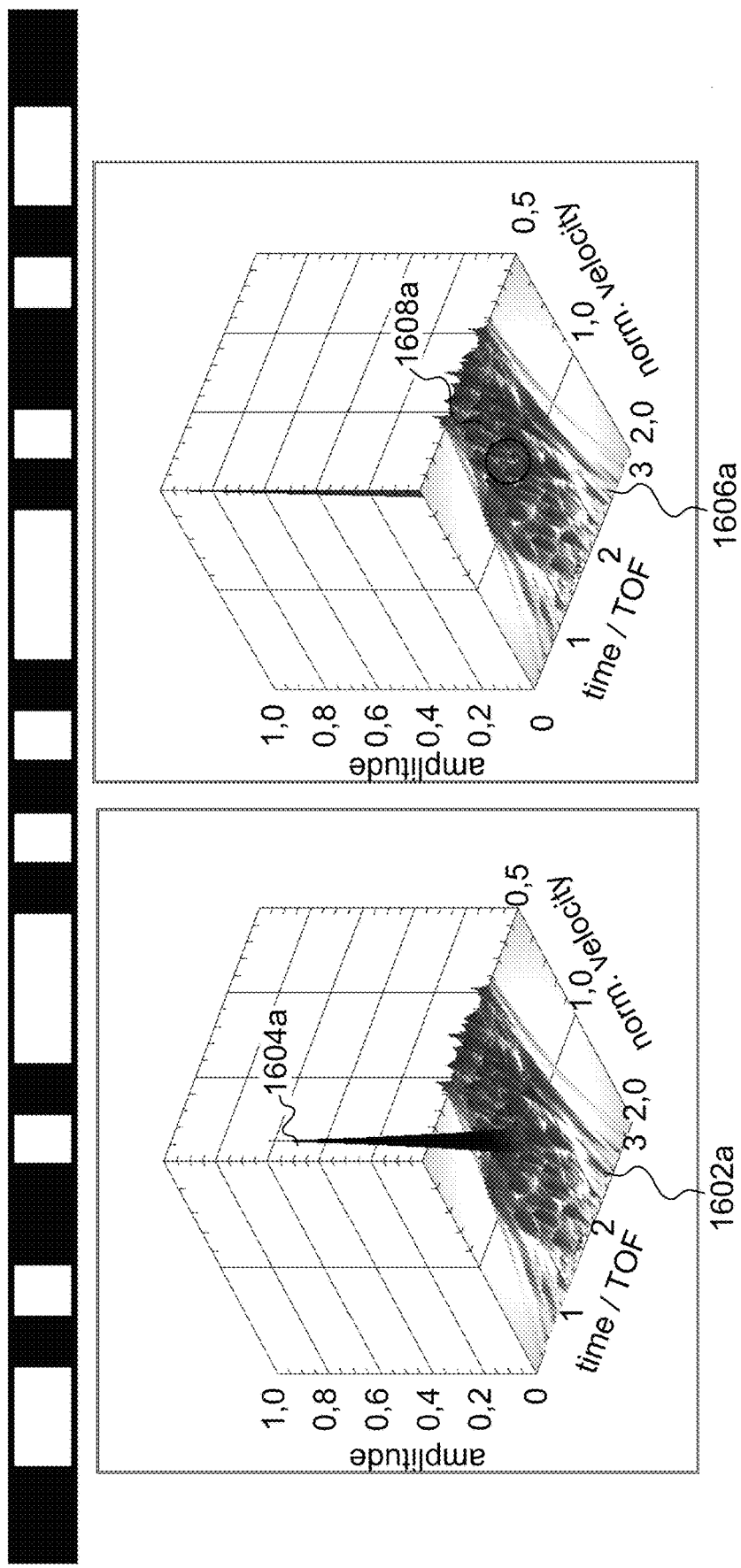

FIG. 16a and FIG. 16b show cutting out the main lobes for determining the cleaned-up correlation functions in embodiments exemplarily for ULABS-Q2DPs31(16,#1). 1602a and 1602b show the correlation functions ULABS-Q2DPs31(16,#1) with the main lobes 1604a and 1604b. 1606a and 1606b show the cleaned-up correlation functions with the vacancies of the removed main lobes 1608a and 1608b.

Figure 17A:
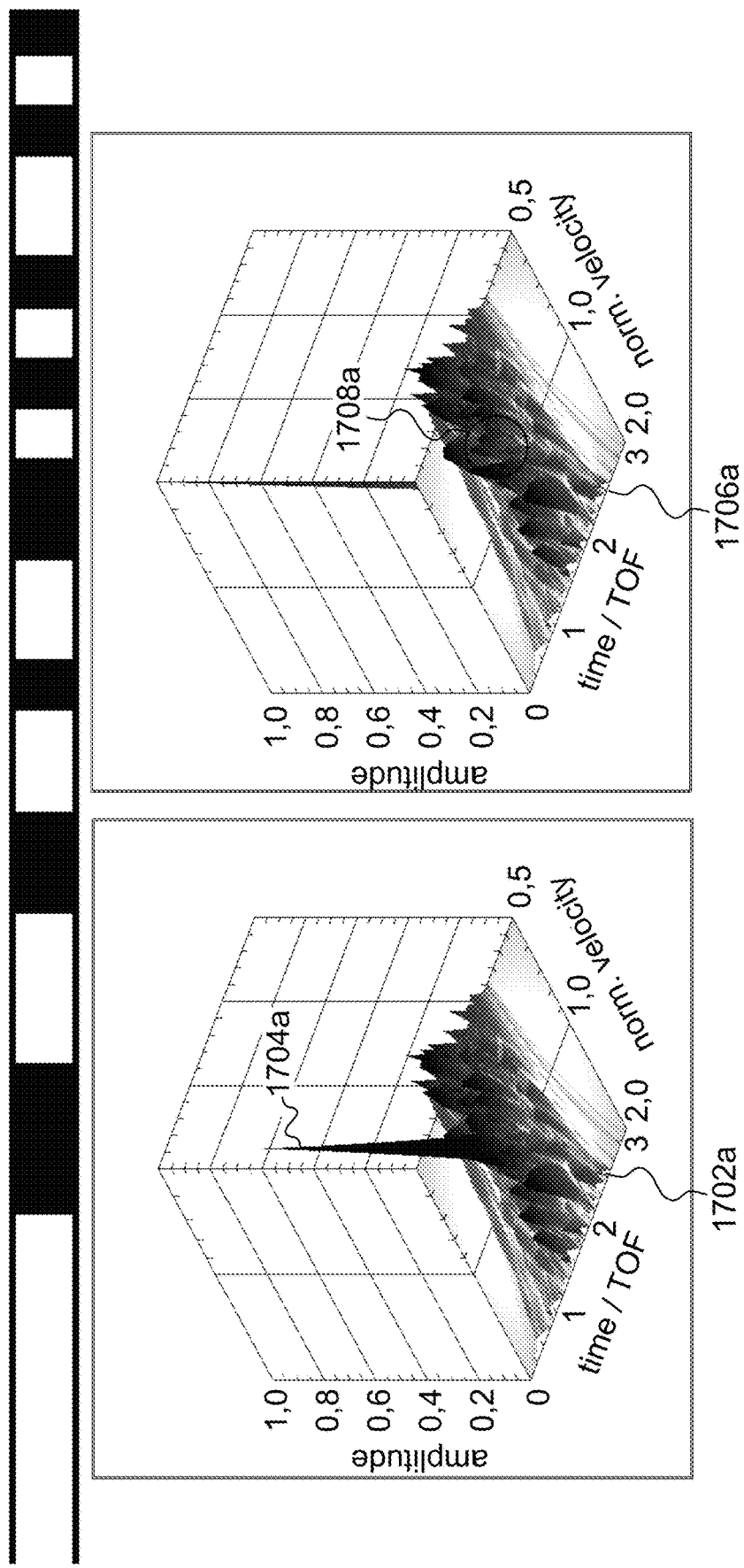
FIGS. 17a and 17b show cutting out the main lobes for determining the cleaned-up correlation functions in embodiments for LABS-Q2DPs31(19,#1)
Figure 17B:
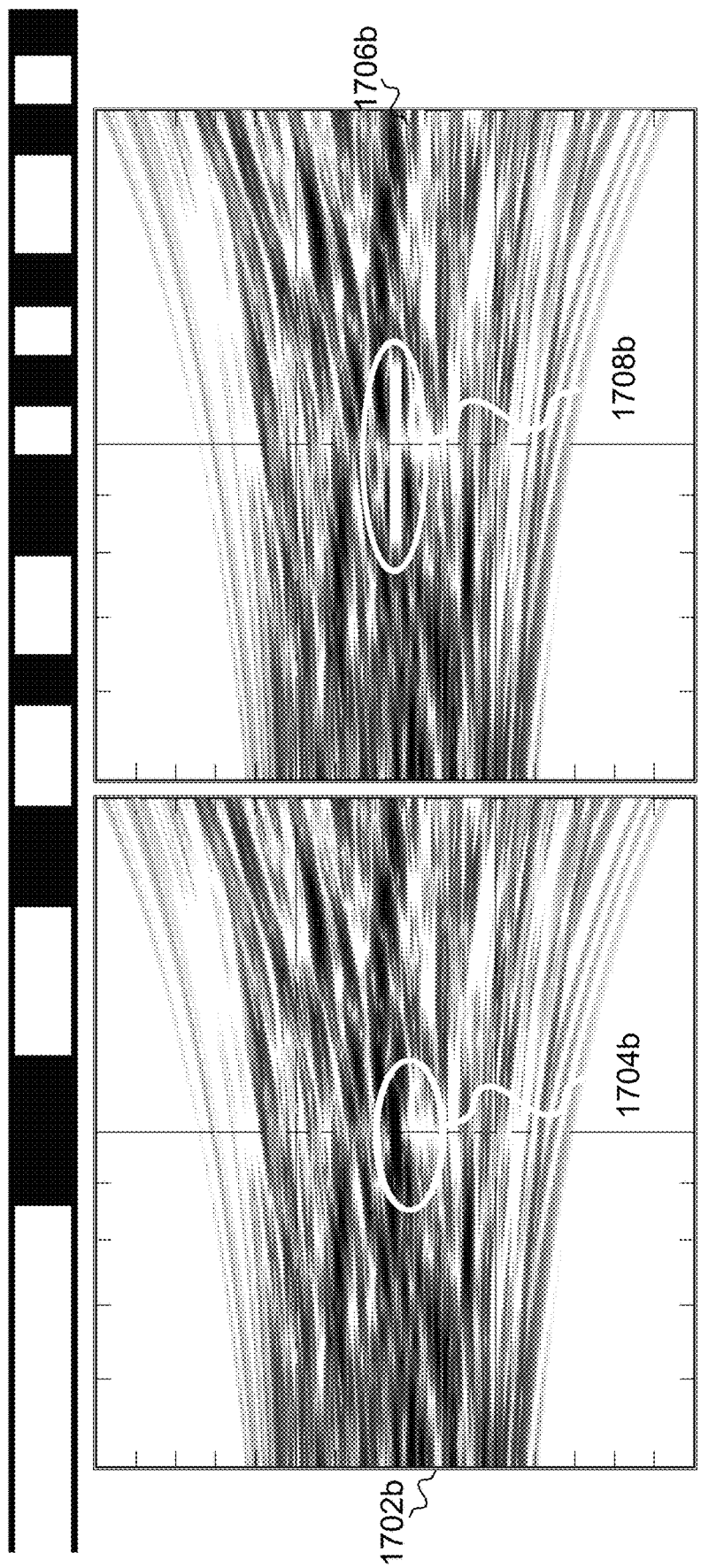

FIG. 17a and FIG. 17b show cutting out the main lobes for determining the cleaned-up correlation functions in embodiments for LABS-Q2DPs31(19,#1). 1702a and 1702b show the correlation functions LABS-Q2DPs31(19,#1) with the main lobes 1704a and 1704b. 1706a and 1706b show the cleaned-up correlation functions with the vacancies of the removed main lobes 1708a and 1708b.

From the amount of remaining correlation values $[c_q]$ and $[c_q]_s$, analog to equation (15) the characteristic values 2DPSLR for criterion 1 and 2DPSLRs for criterion 2 may each be calculated which evaluate the amplitude of the highest side lobe:

$$2DPSLR = \max([c_q^2])$$

$$2DPSLRs = \max([c_q^2]_s) \quad (25)$$

For both criteria it may each be counted how many correlation values were taken from the correlation matrix for the main lobe to calculate the average values analog to equation (16) as a further characteristic variable:

$$2DISLR = \frac{\Sigma_q c_q^2}{K_{NK}}, c_q \text{ ausgewählt nach Kriterium 1}, \quad (26)$$

$$2DISLR_s = \frac{\Sigma_q c_q^2}{K_{NKs}}, c_q \text{ ausgewählt nach Kriterium 2},$$

wherein $K_{NK}$ and $K_{NKs}$ each indicate the number of remaining correlation values.

Again, considering the signal-to-noise gain $SNR_{Gain}$ (see equation (18)) different quality index numbers may be calculated:

$$Q2DI = \frac{SNR_{Gain}}{2DISLR} \quad (27)$$

$$Q2DIs = \frac{SNR_{Gain}}{2DISLRs}$$

and $$Q2DP = \frac{SNR_{Gain}}{2DPSLR} \quad (28)$$

$$Q2DPs = \frac{SNR_{Gain}}{2DPSLRs}$$

In at least some embodiments, the greatest size maximum may be based on 2DPSLR, 2DPSLRs, Q2DP and/or Q2DPs. In at least some embodiments the sum of the side lobes may be based on 2DISLR, 2DISLRs, Q2DI and/or Q2DIs.

A complete search in all codes up to the length L=33 resulted in that numerous unipolar codes exist which are better suitable for the use in RMF (and comparable applications utilizing unipolar codes) using those criteria. For example, these codes/sequences, in embodiments of light detection and ranging (LIDAR) in which pulse sequences which are temporally modulated are used or for radar applications in which no bipolar encoding is possible.

Figure 18:
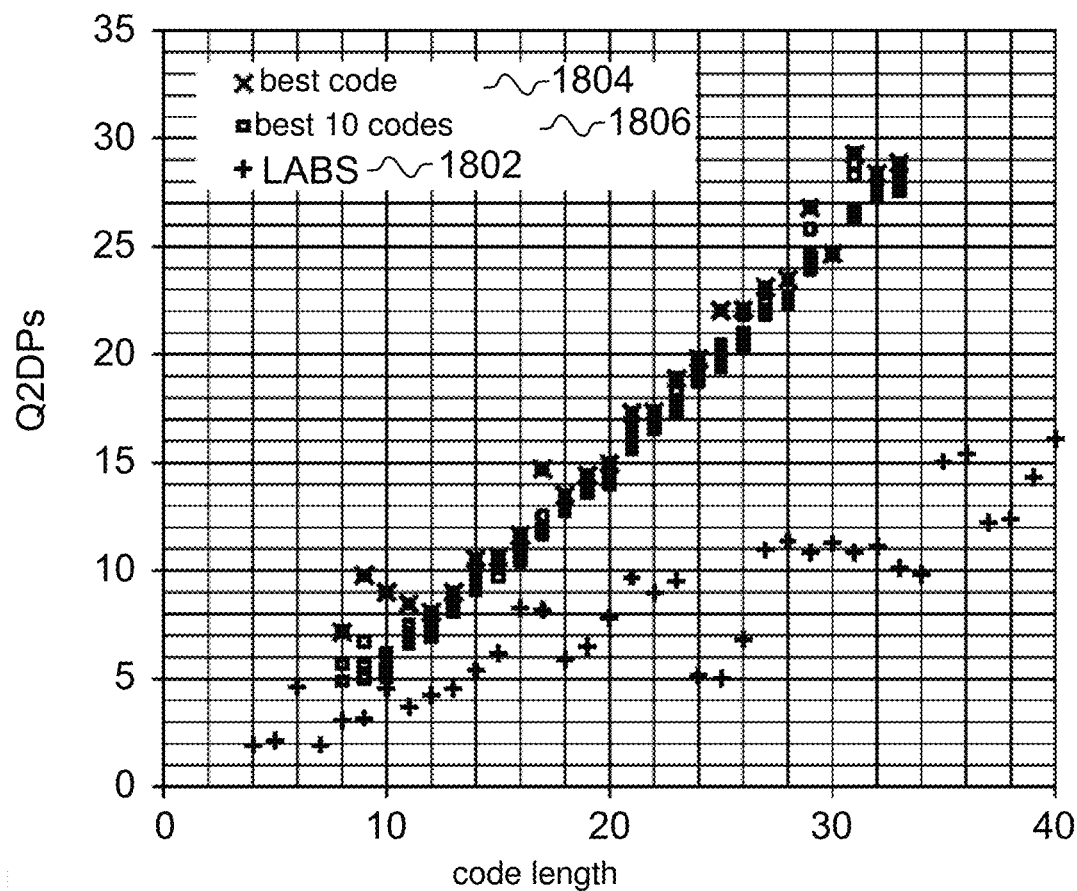
FIG. 18 shows a comparison of the quality index number Q2DPs for known LABS and examples from the class of ULABS of embodiments.

FIG. 18 shows a comparison of the quality index number Q2DPs for the known LABS (best LABS: 1802) and the examples from the class of codes "ULABS" from embodiments (best code: 1804, best 10: 1806).

FIG. 19 shows an exemplary list of the best considered sequences each of the class of LABS and ULABS assessed according to the quality index number Q2DPs. 1902 shows the code ID of the codes, 1904 a binary representation of the codes, 1906 the code length, 1908 the number of ones in the binary code, 1910 shows $SNR_{Gain}$ and 1912 the quality index number Q2DPs.

Figure 20:
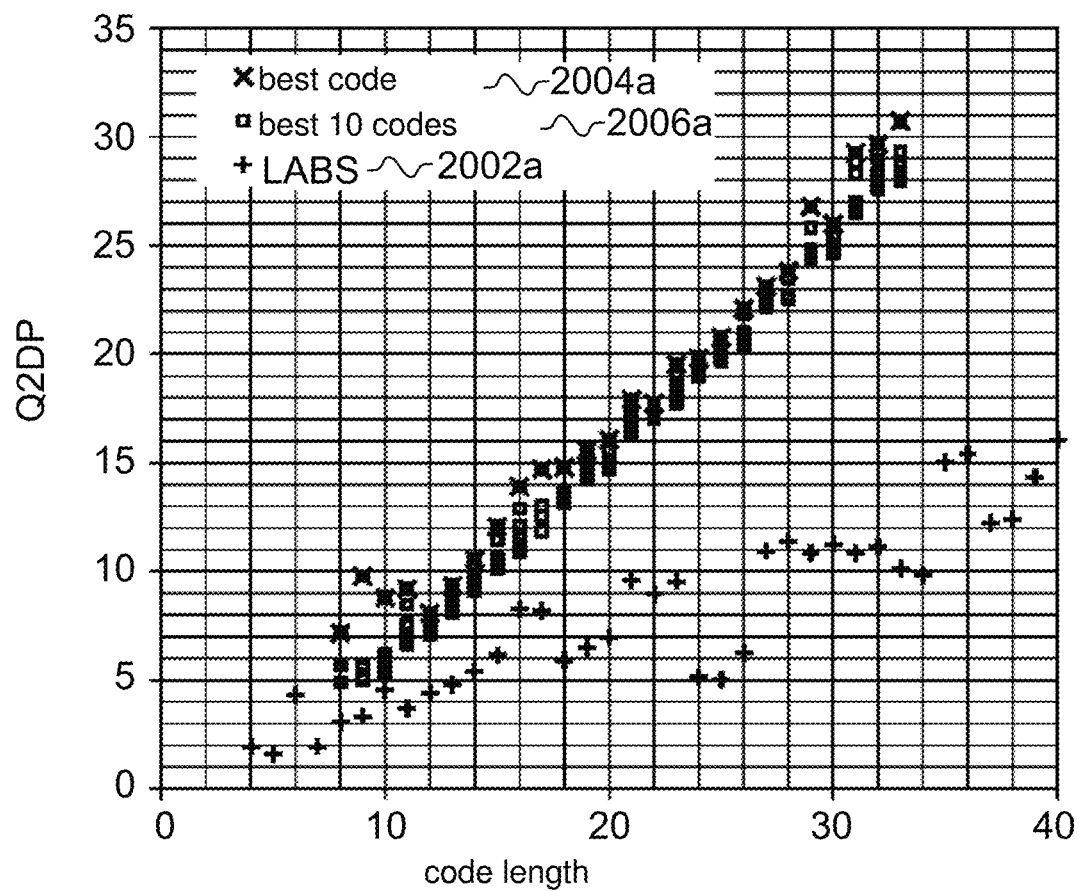
FIG. 20 shows a comparison of the quality index number Q2DP for known LABS and examples from the class of sequences "ULABS" of embodiments.

FIG. 20 shows a comparison of the quality index number Q2DP for the known LABS (best LABS: 2002a) and the examples from the class of codes "ULABS" of the embodiments (best code: 2004a, best 10: 2006a).

FIG. 21 shows an exemplary list of the beset codes each of the class of LABS and ULABS assessed according to the quality index number Q2DP. 2102 shows the code ID of the codes, 2104 a binary representation of the codes, 2106 the code length, 2108 the number of ones in the binary code, 2110 shows $SNR_{Gain}$ and 2112 the quality index number Q2DP.

Figure 22:
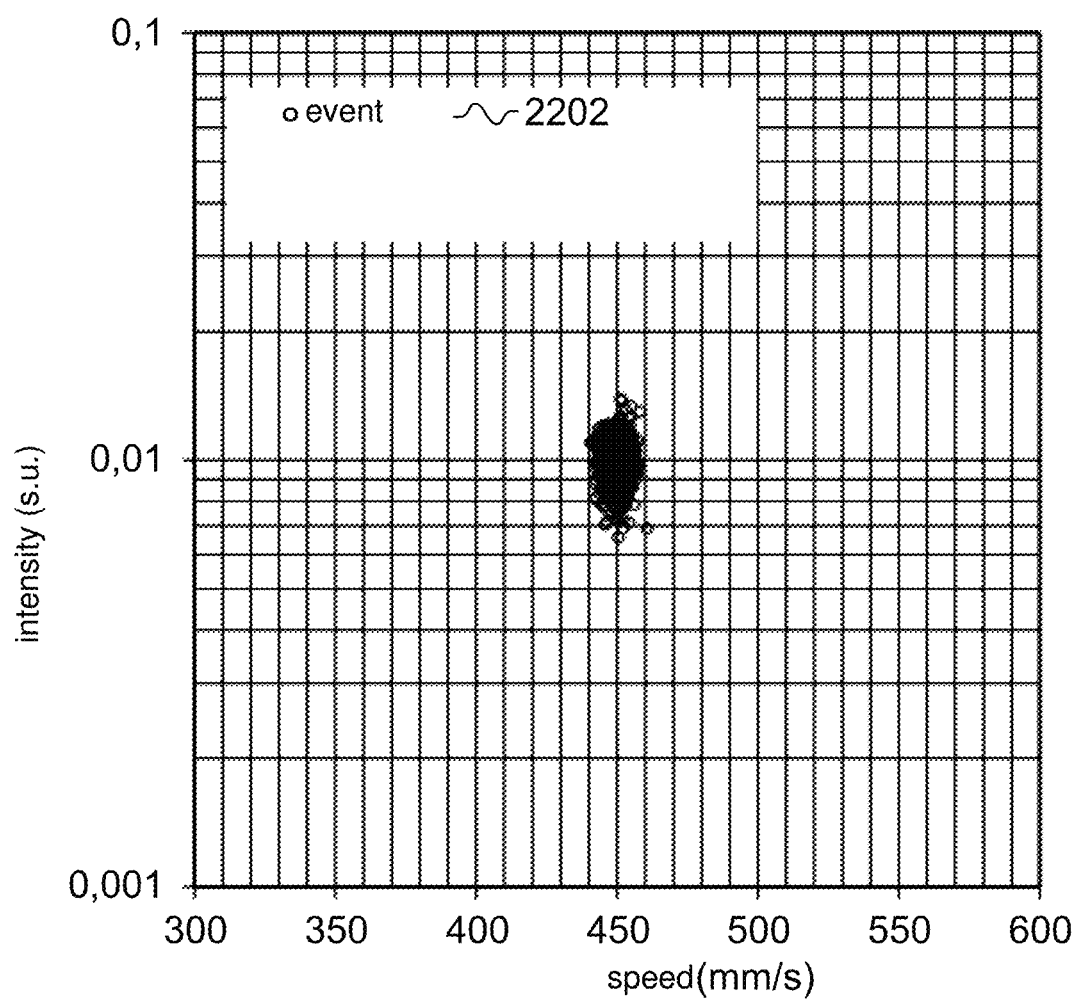
FIG. 22 shows an exemplary input distribution.

For comparing the quality of selected codes in embodiments, using simulated events the detection rate and the erroneous detection rate were determined based on side lobes and in noise. This comparison was done using an input distribution uniform for all considered codes (FIG. 22). The input distribution in embodiments consist of 1000 particle signals 2202 with a Gaussian distributed amplitude (0.01+−0.002) and speed (450+−5 mm/s). For each considered code, thus a raw signal was generated and white noise was each added with a standard deviation of 0.002. The raw signals are consequently only different in the component of the useful signal which follows the respectively considered code.

The raw signals were each correlated with balanced filter banks which cover a speed range from 300 mm/s to 600 mm/s. The event detection was executed by a uniform threshold value factor of 1.3. In a time window of double the runtime of the particle transported at 300 mm/s through the measurement zone, the average amplitude of all maxima is determined in the squared correlation matrix. A maximum which is higher than the average value by the threshold value factor is regarded as an event in embodiments. FIG. 23, FIG. 24, FIG. 25 and FIG. 26 show the detected events of embodiments for the respective codes. Apart from the codes listed in the above tables, further B13Man26(13) was included for comparison. This code is gathered from the Barker 13 code (1111100110101) via a Manchester transformation (1→01, 0→10) and consequently has the length 26.

In at least some embodiments, the threshold value factor was uniformly chosen and is set so that all codes correctly detect more than 99% of the events. In embodiments, all sequences alike enable a detection of events at the noise threshold. This is unproblematic as the same may be sorted out via a global amplitude threshold value. It is noted, however, that the code Q2DPs26(15,#2) (FIG. 24) shows by far the least erroneous detections in embodiments. For this code it may further be possible to detect further events between noise threshold and amplitude of the input distribution. Other sequences of embodiments may fail here as the erroneous detections by side lobes may hide wide amplitude and speed ranges.

Figure 23:
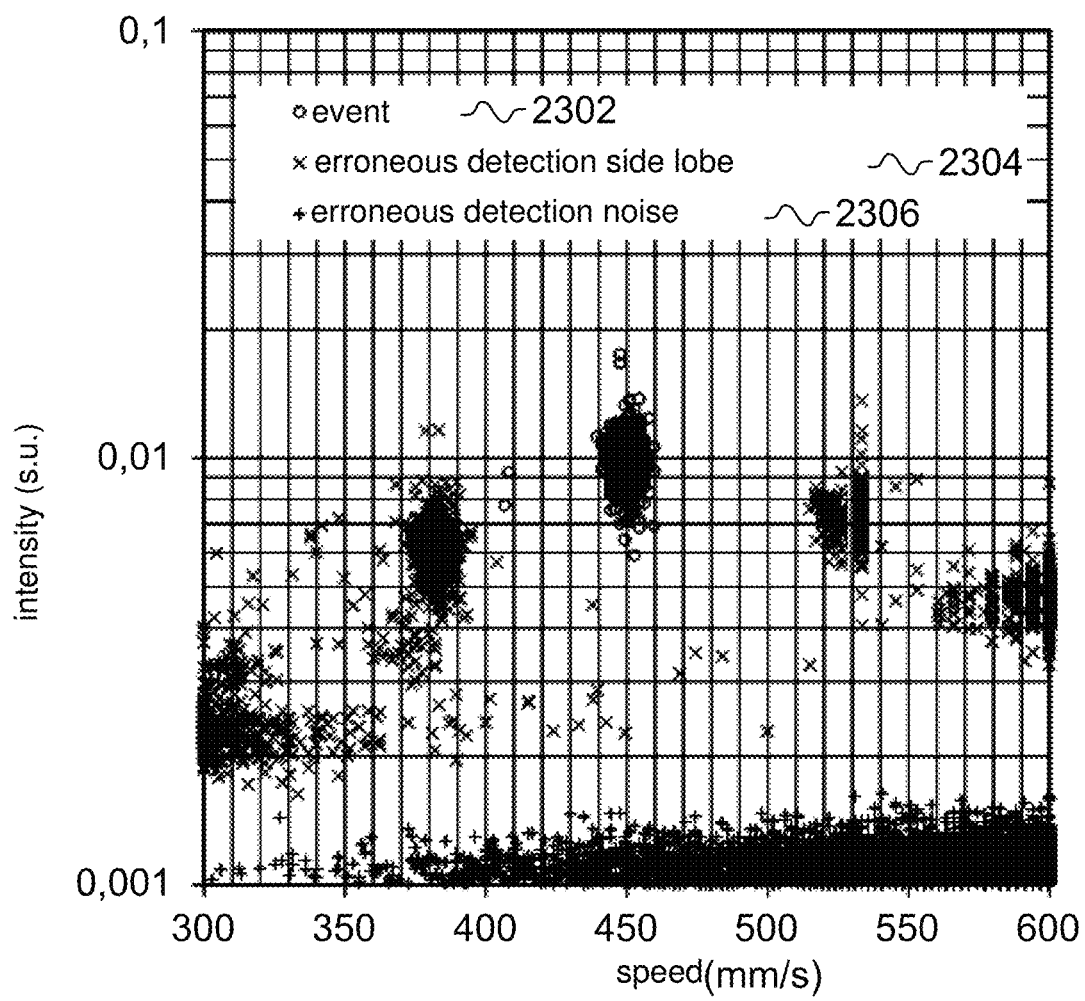
FIG. 23 shows an exemplary output distribution for LABS26(16,#2) with a positive detection rate of 99.6%.
Figure 24:
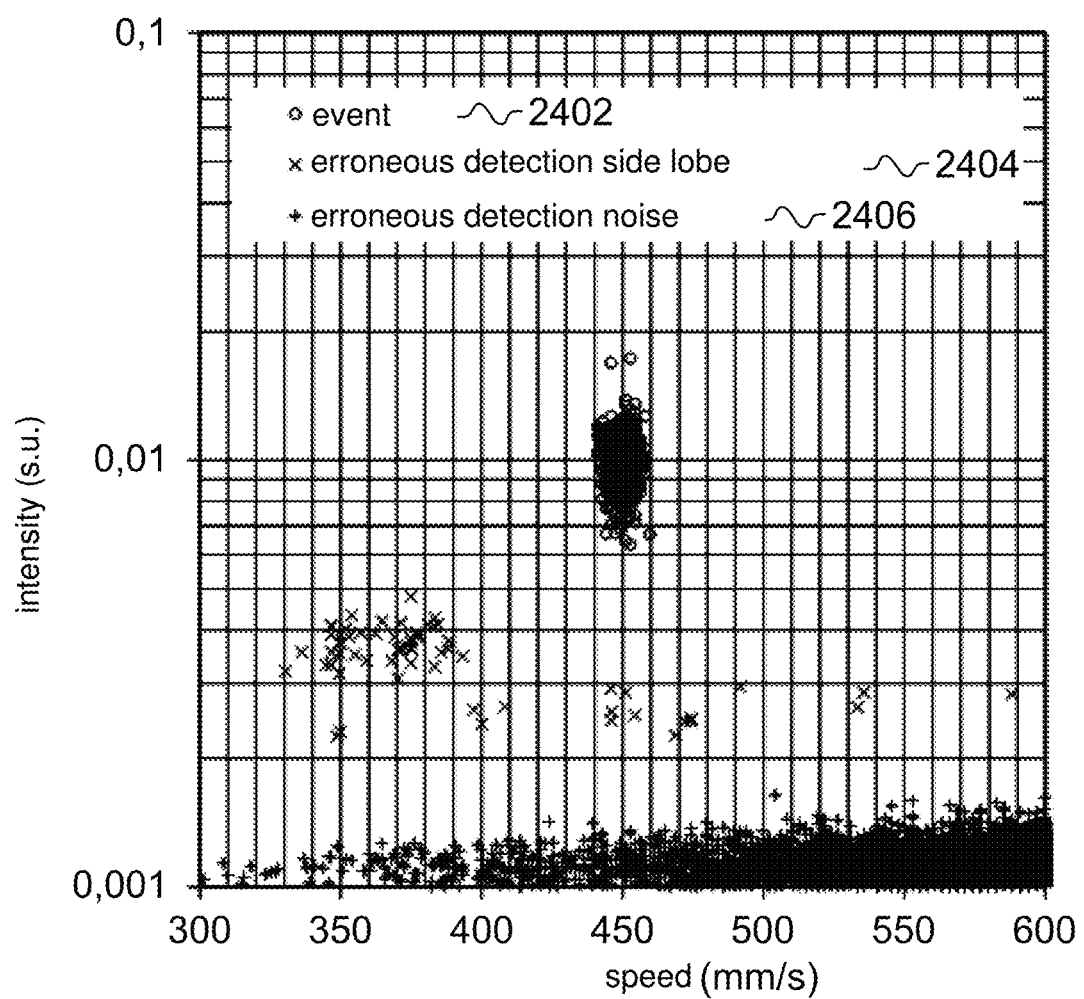
FIG. 24 shows an exemplary output distribution for Q2DPs26(15,#2) with a positive detection rate of 99.8%.
Figure 25:
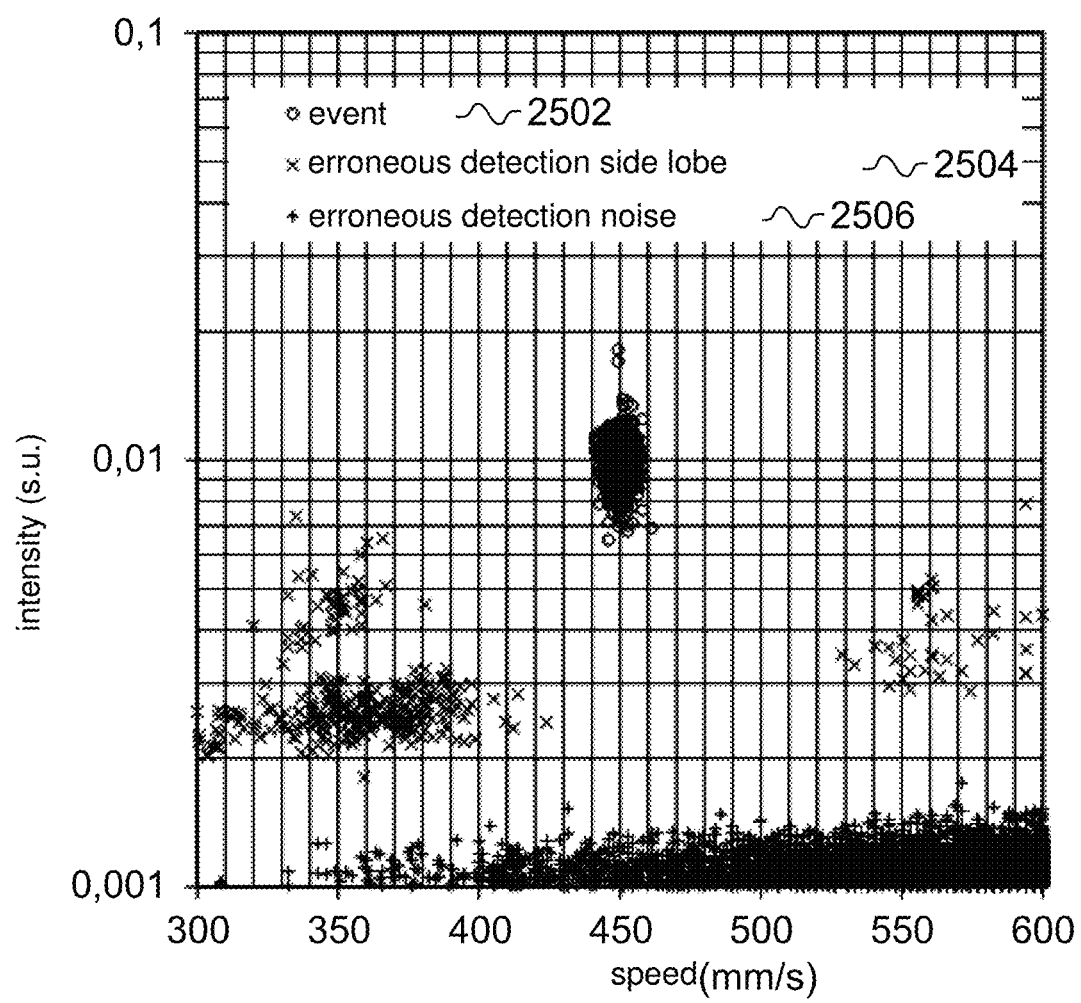
FIG. 25 shows an exemplary output distribution for Q1DI26(14,#1) with a positive detection rate of 99.8%.
Figure 26:
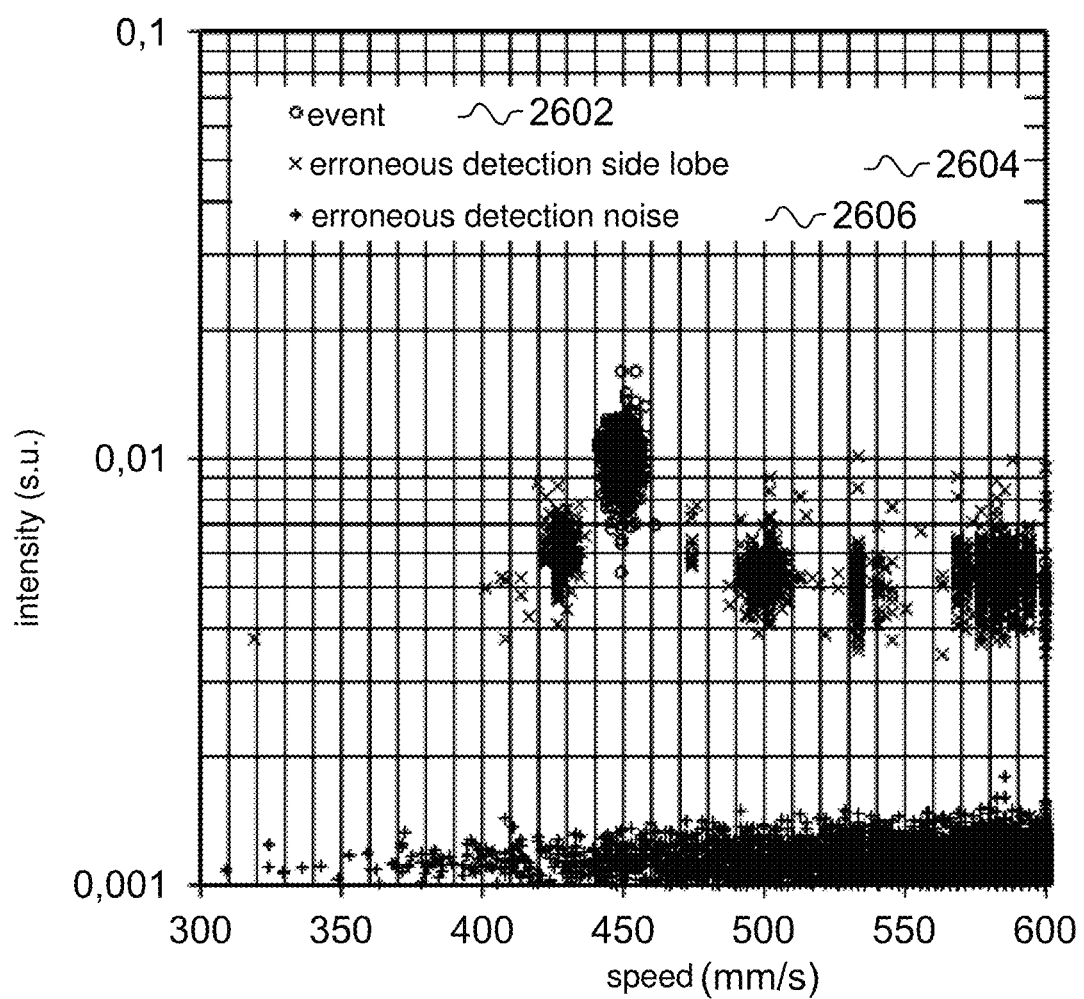
FIG. 26 shows an exemplary output distribution for B13Man26(13) with a positive detection rate of 99.8%.

FIG. 23 shows an exemplary output distribution for the LABS26(16,#2) with a positive detection rate of 99.6%. 2302 (analogously 2402, 2502, 2602) shows the events, 2304 (analogously 2404, 2504, 2604) erroneous detections based on a side lobe and 2306 (analogously 2406, 2506, 2606) erroneous detections based on noise. FIG. 24 shows an exemplary output distribution for Q2DPs26(15,#2) with a positive detection rate of 99.8%. FIG. 25 shows an exemplary output distribution for Q1DI26(14,#1) with a positive detection rate of 99.8%. FIG. 26 shows an exemplary output distribution for B13Man26(13) with a positive detection rate of 99.8%.

Figure 27:
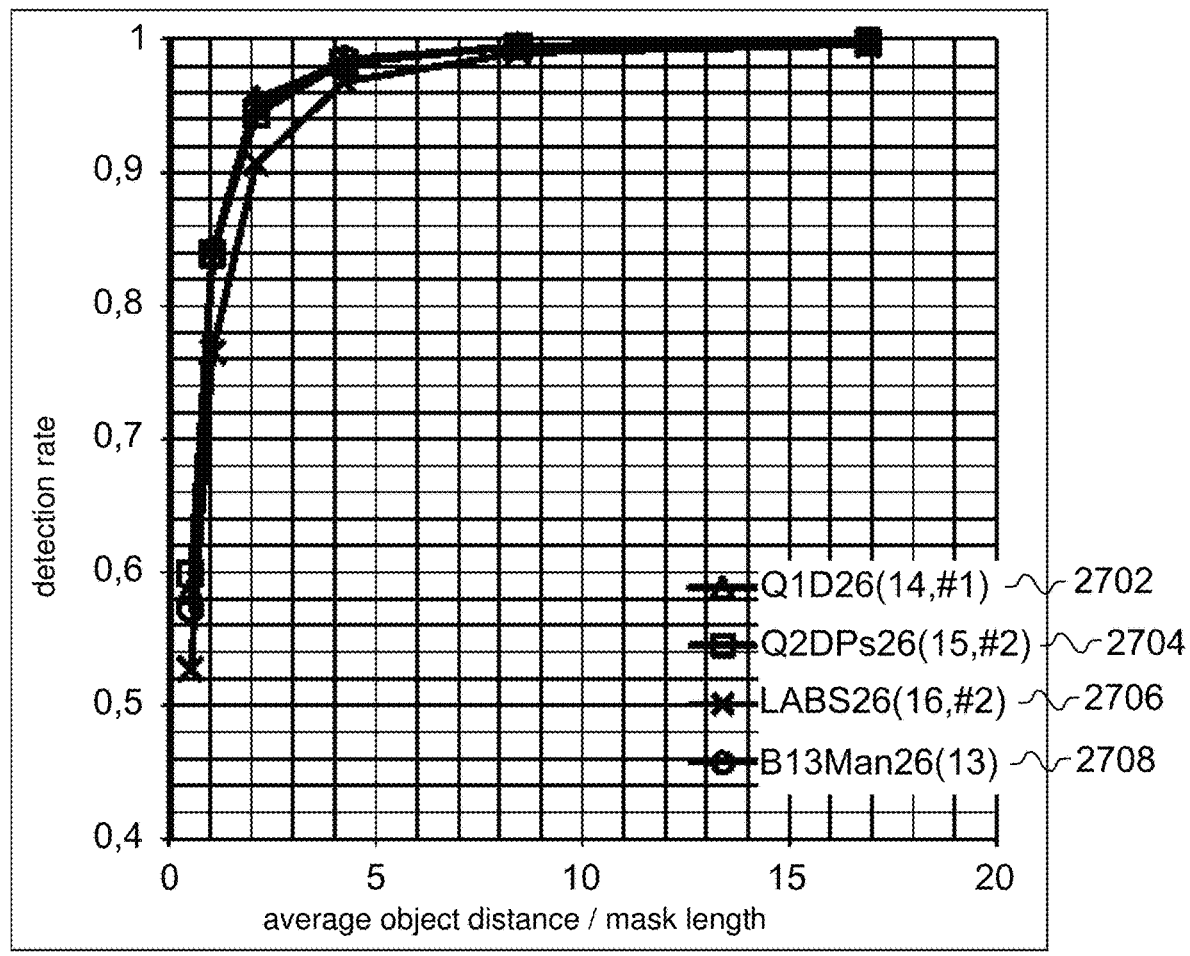
FIG. 27 shows an example of a detection rate as a function of the average particle distance in units of mask length.

If the average temporal distance of the events in the input distribution is reduced, in embodiments for all codes the detection rate is decreased as exemplarily illustrated in FIG. 27.

In some embodiments, the already known LABS26 2706 performs worst. The further codes are virtually identical in an exemplary evaluation, wherein the Q2DPs26(15,#2) 2702 shows slight advantages. FIG. 27 exemplarily shows a detection rate as a function of the average particle distance in units of the mask length, for Q1DI26(14, #1) 2702 (analogously 2802, 2902), Q2DPs26(15, #2) 2704 (analogously 2804, 2904), LABS26 (16, #2) 2706 (analogously 2806, 2906) and B13Man26(13) 2708 (analogously 2808, 2908).

Figure 28:
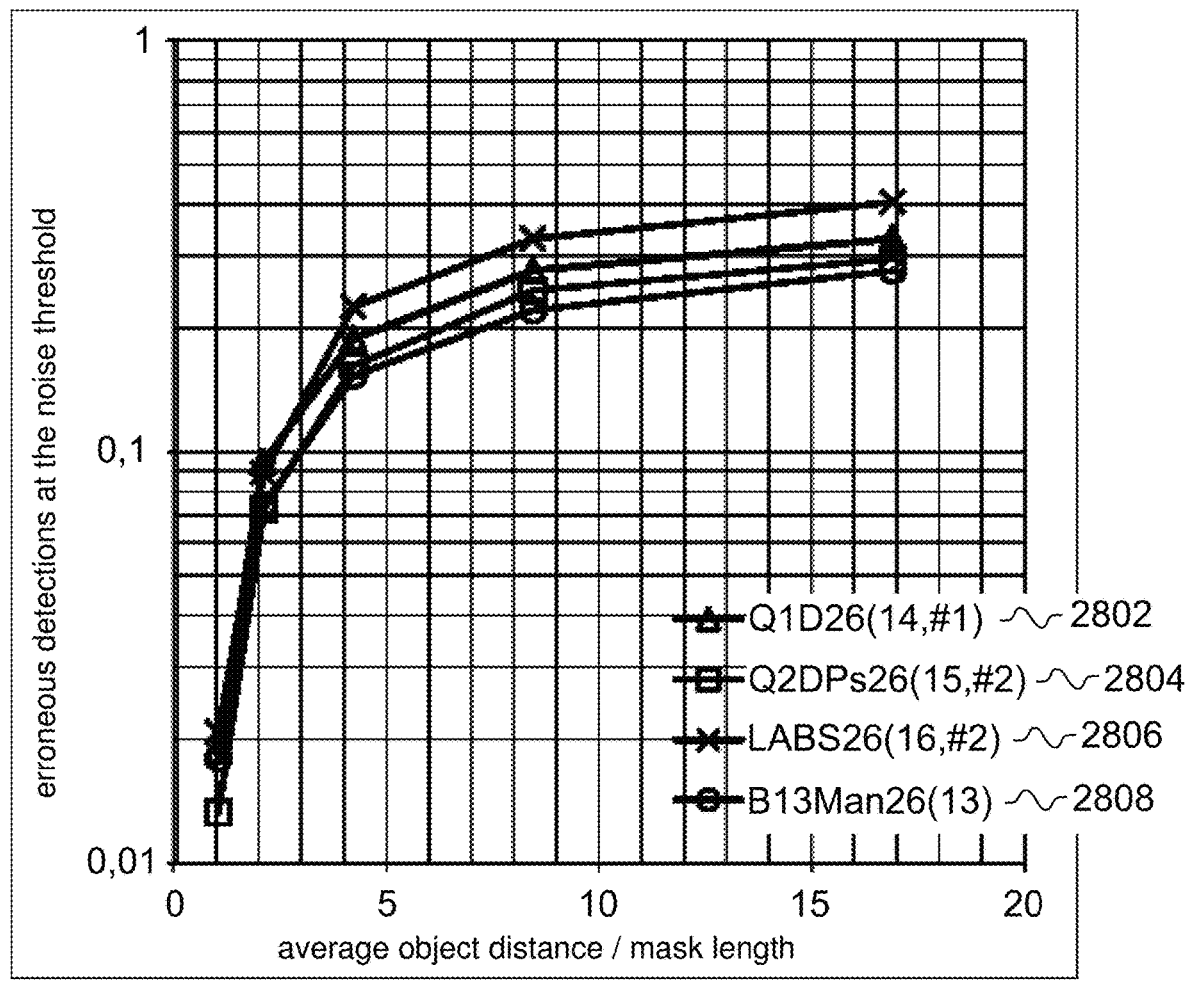
FIG. 28 shows an erroneous detection rate of embodiments in noise as a function of the average particle distance in units of mask length.

The erroneous detection rate in noise behaves largely uniformly for the considered codes in considered embodiments. The decrease with an increasing particle density is consistent as the temporal portions in which there is no particle contribution in the signal decrease with an increasing particle density. There may proportionally be less erroneous detections in noise. FIG. 28 shows the erroneous detection rate of embodiments in noise as a function of the average particle distance in units of mask length.

Figure 29:
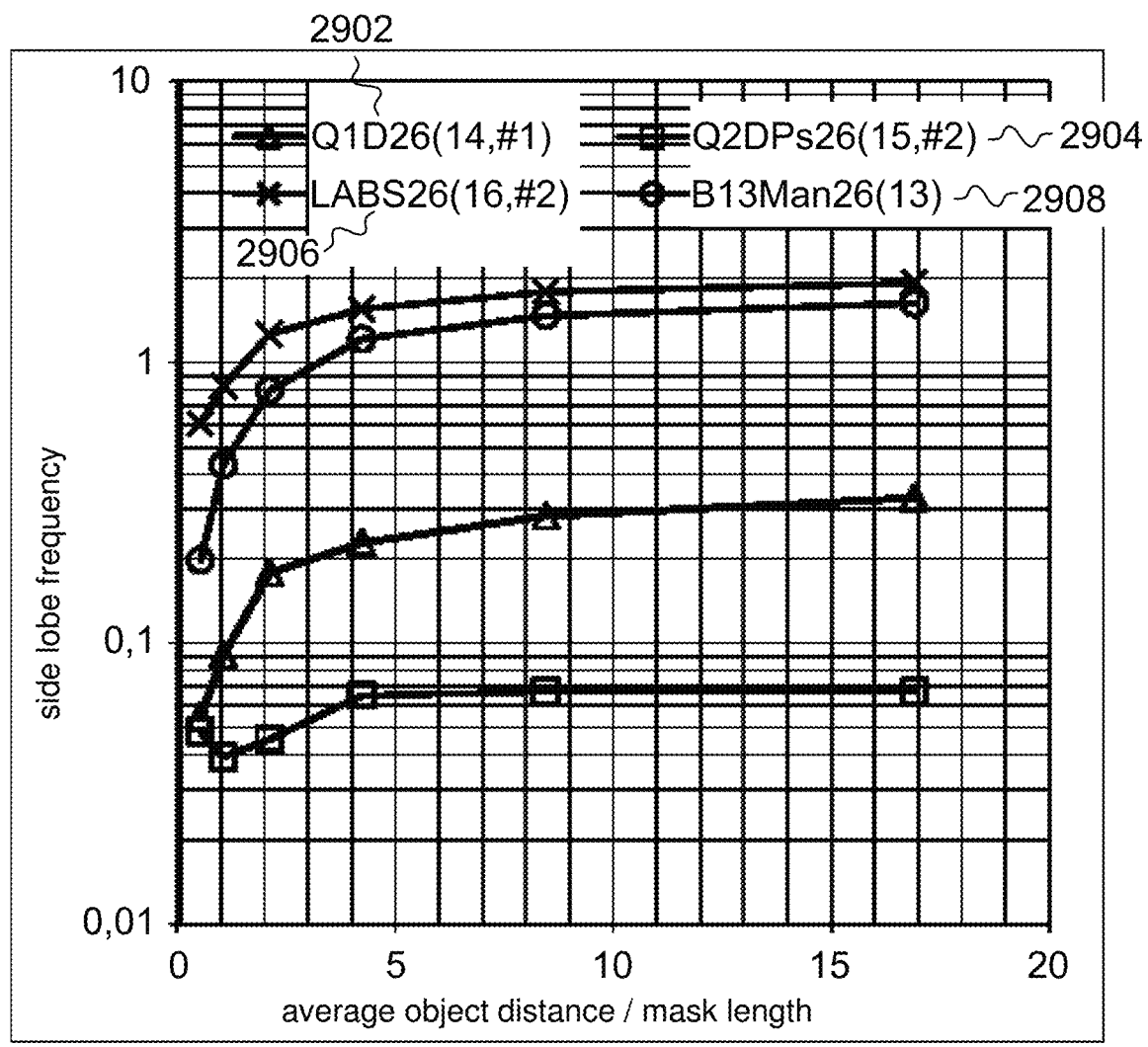
FIG. 29 shows an exemplary comparison of a side lobe frequency.

One important finding in embodiments may now be gathered from the exemplary comparison of the side lobe frequency (FIG. 29). The conventional LABS26(16,#2) 2906 performs worst in exemplary embodiments. B13Man26(13) 2908 and Q1DI26(14,#1) 2902 are better. For both codes a better Q2DPs results than for LABS26(16, #2) 2906, although these codes are not optimized with respect to Q2DPs. Regarding side lobe frequency, Q2DPs26 (15,#2) 2904 performs better, which by far detects the least side lobes in exemplary embodiments. FIG. 29 shows the erroneous detection rate based on side lobes as a function of the average particle distance in units of the mask length.

In a structural size notation for codes it is counted how often a symbol of a code is repeated in direct sequence. With reference to the example of the Barker code 13 this means:

$$[1;1;1;1;1;0;0;1;1;0;1;0;1] \rightarrow [5;2;2;1;1;1;1] \qquad (29)$$

Figure 30:
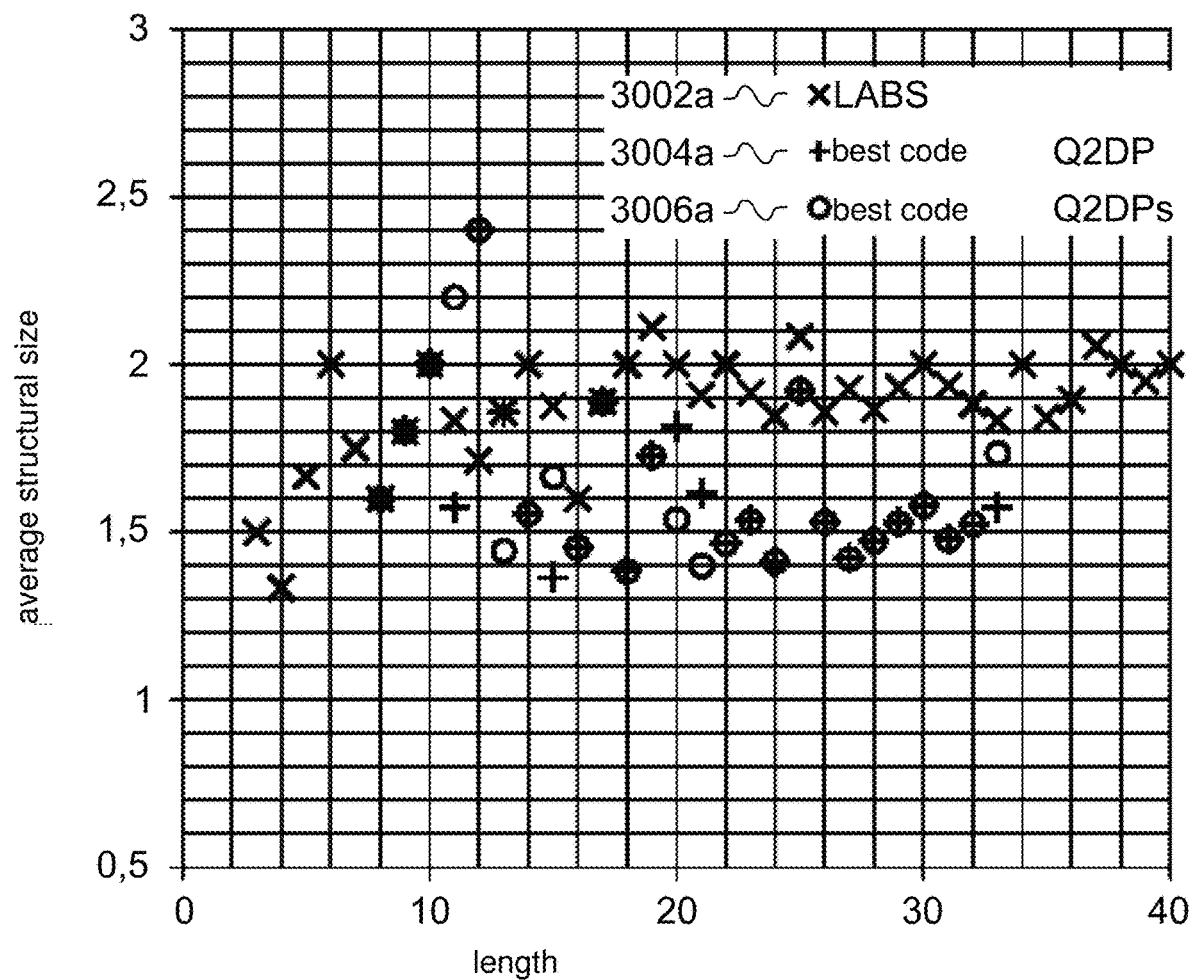
FIG. 30 shows an average structural size for the best examined 2D-codes according to a quality criterion of embodiments and LABS.

The structural size notation is shorter. The average value of the structural sizes is called average structural size. FIG. 30 compares the average structural size for the best 2D codes 3004a and 3006a from embodiments to the LABS 3002a. The average structural size for conventional LABS 3002a is within a range close to 2. For an increasing L (L>40, not illustrated) this connection may become even sharper. Codes with the best Q2DP 3004a and Q2DPs 3006a may for example preferably be found at 1.5 to 1.6. This may be used as a criterion according to which a computational module, like e.g. the computational module 24, may not calculate the values Q2DP and Q2DPs which are complex to be determined for all codes, may restrict the plurality of possible sequences or may restrict the subset of possible sequences in case of high code lengths. FIG. 30 shows a connection between average structural size and code length compared for the best codes according to the criteria Q2DP 3004a and Q2DPs 3006a as well as for LABS 3002a.

In case of experimental setups (e.g. array detectors) in which several modulation sequences may be imprinted on one event, it may be appropriate to use sequences with different characteristics in order to improve the detection. Thus, for example, a particle with an optimum 2D LABS may be detected and subsequently using a strictly periodical sequence (like 010101010101010 . . . ) the speed may be determined.

Figure 31:
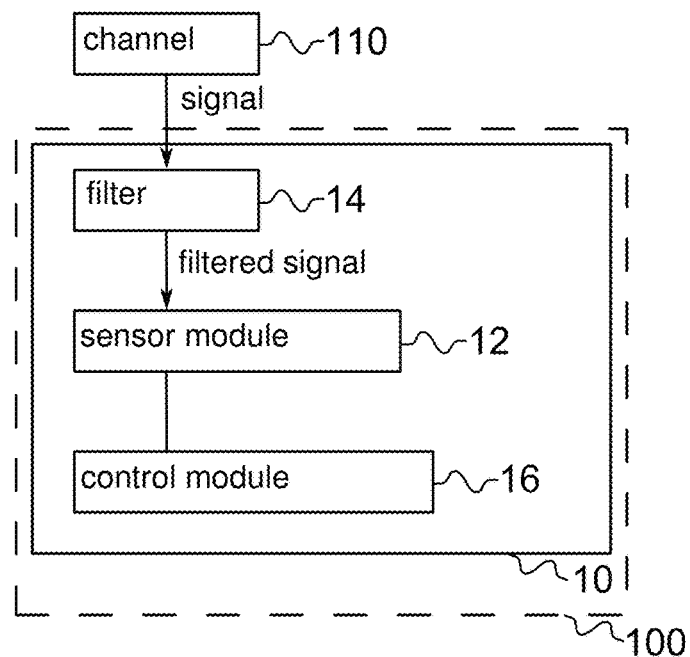
FIG. 31 shows an embodiment of a device for a cytometer.

FIG. 31 shows an embodiment of a device 10 for a cytometer 100. The device 10 is implemented for providing information on one or several cells in a medium in a channel 110. The device includes a sensor module 12 which is implemented to detect a filtered signal. The filtered signal is influenced by the cells streaming through the channel 110.

In embodiments, the sensor module 12 may for example correspond to a light-sensitive sensor, a photodetector, a photo sensor, a radiation detector or a radiation sensor. In at least some embodiments, the sensor module 12 may be implemented to detect light signals. Alternatively or additionally, the sensor module 12 may be implemented to detect signals from electromagnetic waves. In at least some embodiments, the sensor module 12 may include one or several sensor units.

The channel 110 may, for example, correspond to a liquid channel or a flow cytometry channel. The channel 110 may for example be implemented to transport or conduct the medium which may for example correspond to a suspension or a fluid which includes the one or several cells along the sensor module 12. The medium may for example be transported through the channel by means of a pump module. In at least some embodiments, the cytometer 100 may correspond to a flow cytometer and/or a fluorescence-based flow cytometer. In some embodiments, the cytometer 100 may for example correspond to a cytometer 100 with sorting functionality, for example based on fluorescence-activated cell sorting (FACS).

The device 10 further includes a filter 14. The filter 14 is implemented to spatially map a given sequence. The filter 14 is implemented to provide the filtered signal based on the sequence and a signal influenced by the cells streaming through the channel. In at least some embodiments, the filter 14 may correspond to a filter mask. The filter mask may for example be implemented to spatially shade the signal influenced by the cells streaming through the channel in order to provide the filtered signal. The signal may, for example, be based on the one or several cells which are for example excited by a stimulation module, for example by means of fluorescence based on a laser. The filter mask may be implemented to spatially shade the light emitted by the fluorescence based on the sequence in order to provide the filtered signal. Alternatively or additionally, the filter 14 may shade the stimulation module so that for example the one or several cells are excited based on the sequence and/or the filter may include one or several stimulation sources which are implemented to excite the one or several cells based on the sequence in order to provide the filtered signal.

The device 10 further includes a control module 16 which is implemented to provide the information on the one or several cells based on a correlation analysis of the detected filtered signal and at least one temporal scaling of the sequence. The sequence describes temporally successive signal states. The sequence of the signal states within the sequence is selected such that a side lobe in a correlation function of the sequence comprising the at least one temporal scaling of the sequence is reduced as compared to a side lobe which may maximally be acquired in the correlation function by different arrangements of the signal states in the sequence.

In embodiments, the control module 16 may correspond to any controller or processor or a programmable hardware component. For example, the control module 16 may also be realized as software which is programmed for a corresponding hardware component. In so far, the control module 16 may be implemented as a programmable hardware comprising a correspondingly adapted software. Here, any processors, like digital signal processors (DSPs) may be used. Embodiments here are not restricted to a certain type of processor. Any processors or also several processors are possible for implementing the control module 16.

In at least some embodiments, a series of signal states may be selected such within the at least one sequence that a sum which is based on side lobes of the correlation function of the sequence comprising the at least one temporal scaling of the sequence is reduced as compared to a sum which may maximally be acquired by different arrangements of the signal states in the sequence, wherein the sum is based on side lobes resulting from the different arrangement.

The series of the signal states within the at least one sequence may be selected such that a greatest side lobe of the correlation function of the sequence comprising the at least one temporal scaling of the sequence is reduced as compared to a greatest side lobe which may maximally be acquired by different arrangements of the signal states in the sequence.

In some embodiments, the sum which is based on the side lobes may be below a first threshold value. The greatest side lobe may, for example, be below a second threshold value.

In at least some embodiments, the first threshold value may correspond to a second-lowest sum which is based on side lobes of correlation functions of possible sequences. The second threshold value may, for example, correspond to a greatest side lobe of a sequence with a second-lowest greatest side lobe of the correlation functions.

In at least some embodiments, the sequence may correspond to a unipolar sequence. In at least some embodiments, the filter 14 may be balanced.

More details and aspects of the device 10 (e.g. sequence, correlation function, temporal scaling, temporally successive signal states, first threshold value, second threshold value, unipolar sequence) are mentioned in connection with the concept or examples which were previously described (e.g. FIGS. 1 to 30). The device 10 may comprise one or several additional optional features corresponding to one or several aspects of the proposed concept or the described examples as described above or below.

Figure 32:
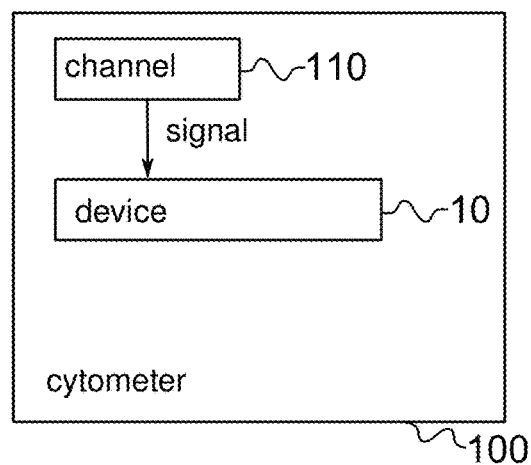
FIG. 32 shows a block diagram of an embodiment of a cytometer.

FIG. 32 shows a block diagram of an embodiment of a cytometer 100. The cytometer comprises a device 10 and a channel 110. The device 10 is implemented to provide information on one or several cells in a medium in the channel 110 to the cytometer 100.

More details and aspects of the cytometer 100 (e.g. cytometer 100, device 10, channel 110) are mentioned in connection with the concept or examples which were described above (e.g. FIGS. 1 to 31). The cytometer 100 may comprise one or several additional optional features corresponding to one or several aspects of the proposed concept or the described examples as described above or below.

Figure 33:
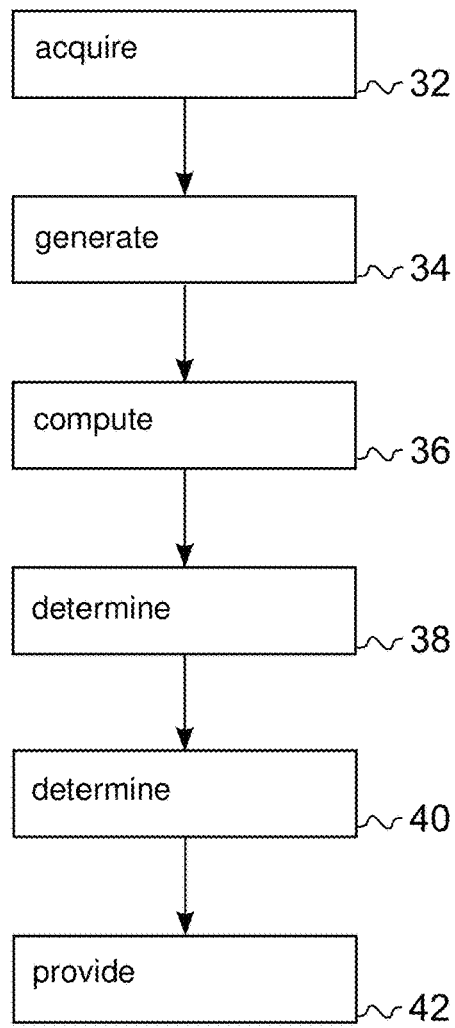
FIG. 33 shows a flowchart of a method for providing information on at least one sequence.

FIG. 33 shows a flowchart of a method for providing information on at least one sequence. The at least one sequence describes temporally successive signal states. The method includes receiving 32 information on a number of the signal states and generating 34 a plurality of possible sequences based on the information on the number of the signal states. The method further includes calculating 36 correlation functions between a sequence and at least one temporal scaling of the sequence for at least a subset of the possible sequences. A correlation function includes a main lobe and one or several side lobes. The method further includes determining 38 the at least one sequence based on the correlation functions. The order of the signal states within the at least one sequence is selected such that a side lobe in a correlation function of the sequence comprising the at least one temporal scaling of the sequence is reduced as compared to a side lobe which may maximally be acquired in a correlation function by different arrangements of the signal states in the sequence. The method further includes determining 40 the information on the at least one sequence based on the at least one sequence and providing 42 the information on the at least one sequence.

Figure 34:
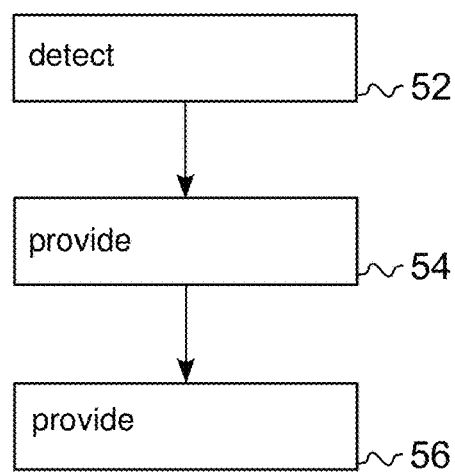
FIG. 34 shows a flowchart of a method for providing information on one or several cells in a medium in a channel.

FIG. 34 shows a flowchart of a method for providing information on one or several cells in a medium in a channel 110. The device includes detecting 52 a filtered signal. The filtered signal is influenced by cells streaming through the channel 110. The method further includes providing 54 the filtered signal based on a predetermined sequence, a signal influenced by the cells streaming through the channel and a spatial mapping of the sequence. The method further includes providing 56 the information on the one or several cells based on a correlation analysis of the detected filtered signal and at least one temporal scaling of the sequence. The sequence describes temporally successive signal states. The order of the signal states within the sequence is selected such that the side lobe in a correlation function of the sequence comprising the at least one temporal scaling of the sequence is reduced as compared to a side lobe which may maximally be acquired in the correlation function by different arrangements of a signal state in the sequence.

A further embodiment is a computer program for executing at least one of the above-described methods when the computer program is executed on a computer, a processor or a programmable hardware component. A further embodiment is a digital storage medium which is machine- or computer-readable and comprises electronically readable control signals which cooperate with a programmable hardware component so that one of the above-described methods is executed.

Features disclosed in the above description, the following claims and in the attached Figures may be of importance and implemented both individually and also in any combination for the realization of an embodiment in its different implementations.

Although some aspects were described in connection with a device it is obvious that those aspects also represent a description of the corresponding method, so that a block or a member of a device may also be regarded as a corresponding method step or as a feature of a method step. Analog to this, aspects described in connection with or as a method step also represent a description of a corresponding block or detail or feature of a corresponding device.

Depending on the certain implementation requirements, embodiments of the invention may be implemented in hardware or in software. The implementation may executed be using a digital storage medium, like e.g. a floppy disk, a DVD, a Blu-Ray disc, a CD, an ROM, a PROM, an EPROM, an EEPROM or a flash memory, a hard disc or any other magnetic or optical memory on which electronically readable control signals are stored which may cooperate or do cooperate with a programmable hardware component so that the respective method is executed.

A programmable hardware component may be formed by a processor, a computer processor (CPU=central processing unit), a graphics processing unit (GPU), a computer, a computer system, an application-specific integrated circuit (ASIC), an integrated circuit (IC), a system on chip (SOC), a programmable logics element or a field programmable gate array with a microprocessor (FPGA).

The digital storage medium may thus be machine- or computer-readable. Some embodiments further include a data carrier comprising electronically readable control signals which are able to cooperate with a programmable computer system or a programmable hardware component such that one of the methods described herein is executed. An embodiment is consequently a data carrier (or a digital storage medium or a computer-readable medium) on which the program for executing one of the methods described herein is recorded.

In general, embodiments of the present invention may be implemented as a program, firmware, computer program or computer program product comprising a program code or as data, wherein the program code or the data are effective in so far as to execute one of the methods when the program runs on a processor or a programmable hardware component. The program code or the data may for example be stored on a machine-readable carrier or data carrier. The program code or the data may among others be present as a source code, machine code or byte code or as any other intermediate code.

One further embodiment is a data stream, a signal sequence or a sequence of signals which for example represent the program for executing one of the methods described herein. The data stream, the signal sequence or the sequence of signals may for example be configured to be transferred via a data communication connection, for example via the internet or another network. Embodiments are consequently also signal sequences representing data which are suitable for a transmission via a network or a data communication connection, wherein the data represents the program.

A program according to one embodiment may implement one of the methods during its execution, for example by reading out memory locations or writing a piece of data or several data into the same, whereby possibly switching processes or other processes are caused in transistor structures, in amplifier structures or in other electrical, optical or magnetic components or components operating according to another functional principle. Accordingly, by reading out a memory location a program may detect, determine or measured data, values, sensor values or other information. Consequently, by reading out one or several memory locations a program may detect, determine or measure variables, values, measured quantities and other information, or cause, initiate or execute an action by writing into one or several memory locations as well as control other devices, machines and components.

Embodiments may for example be used to determine improved codes which may comprise the following advantages:

Significantly reduced erroneous detection rates

Improved detection in case of overlapping signals

Improved sensitivity for signals of low amplitude in case of an overlapping with signals of high amplitude The above-described embodiments merely represent an illustration of the principles of the present invention. It is obvious that modifications and variations of the arrangements and details described herein are obvious to other persons skilled in the art. It is thus the object that the invention is only restricted by the scope of the subsequent patent claims and not by the specific details which were presented herein by the description and the explanation of the embodiments.

Research operations which led to these results were supported by the European Union.

The invention claimed is:

1. A device for providing information on at least one sequence, wherein the at least one sequence describes temporally successive signal states, the device comprising
an interface configured to receive information on a number of the signal states; and
a computational module configured to
generate a plurality of possible sequences based on the information on the number of the signal states,
calculate correlation functions between a sequence and at least a temporal scaling of the sequence for at least a subset of the possible sequences, wherein a correlation function includes a main lobe and one or several side lobes,
determine the at least one sequence based on the correlation functions, wherein the order of the signal states within the at least one sequence is selected such that a side lobe in a correlation function of the sequence comprising the at least one temporal scaling of the sequence is reduced as compared to a side lobe which may maximally be acquired in a correlation function by different arrangements of the signal states in the sequence, and determine the information on the at least one sequence based on the at least one sequence and provide the same via the interface.

2. The device according to claim 1, wherein the computational module is configured to determine the at least one sequence based on the correlation functions, wherein the order of the signal states within the at least one sequence is selected such that a sum which is based on the side lobes of a correlation function of the sequence comprising the at least one temporal scaling of the sequence is reduced as compared to a sum which may maximally be acquired by different arrangements of the signal states in the sequence, wherein the sum is based on side lobes resulting from the different arrangements, and/or wherein the order of the signal states within the at least one sequence is selected such that a greatest side lobe in the correlation function of the sequence comprising the at least one temporal scaling of the sequence is reduced as compared to a greatest side lobe which may maximally be acquired by different arrangements of the signal states in the sequence.

3. The device according to claim 2, wherein computational module is configured to determine the at least one sequence so that the sum which is based on the side lobes is below a first threshold value, and/or wherein the computational module is configured to determine the at least one sequence so that the greatest side lobe is below a second threshold value.

4. The device according to claim 3, wherein the first threshold value corresponds to a second lowest sum which is based on the side lobes of the correlation functions and/or wherein the second threshold value corresponds to a greatest side lobe of a sequence comprising a second-lowest greatest side lobe of the correlation functions.

5. The device according to claim 1, wherein the computational module is configured to determine cleaned-up correlation functions based on the correlation functions, wherein the computational module is configured to reduce a contribution of main lobes in the cleaned-up correlation functions, and wherein the computational module is configured to determine the information on the at least one sequence based on the cleaned-up correlation functions.

6. The device according to claim 5, wherein the computational module is configured to determine a greatest main lobe among the main lobes of the correlation functions, and wherein the computational module is configured to reduce the contribution of the main lobes in the cleaned-up correlation functions via the temporal extent of the greatest main lobe.

7. The device according to claim 6, wherein the computational module is configured to determine and to reduce the contributions of the main lobes in the cleaned-up correlation functions of the temporally-scaled sequences and neighboring temporal scaling of the sequence based on a temporal position of the greatest main lobe and based on the correlation function of the temporally-scaled sequence comprising the greatest main lobe.

8. The device according to claim 1, wherein a sequence comprises an average structural size, wherein a structural size is based on a number of equal successive signal states, and wherein the computational module is configured to generate the plurality of possible sequences based on a target range for the average structural size and/or wherein the computational module is configured to determine the subset of the possible sequences based on the average structural size and/or the target range for the average structural size.

9. The device according to claim 8, wherein the average structural size corresponds to an average of the structural sizes of a sequence, and wherein the target range for the average structural size lies between 1.3 and 1.8.

10. The device according to claim 1, wherein the computational module is configured to determine the plurality of possible sequences as unipolar sequences.

11. The device according to claim 1, wherein a sequence corresponds to a binary sequence and wherein the binary sequence describes temporally equidistant successive signal states.

12. A device for a cytometer for providing information on one or several cells in a medium in a channel, the device comprising a sensor module configured to acquire a filtered signal, wherein the filtered signal is influenced by the cells streaming through the channel, a filter configured to spatially map a predetermined sequence and configured to provide the filtered signal based on the sequence and a signal influenced by the cells streaming through the channel, and a control module configured to provide the information on the one or several cells based on a correlation analysis of the acquired filtered signal and at least a temporal scaling of the sequence, wherein the sequence describes temporally successive signal states and wherein the order of the signal states within the sequence is selected such that a side lobe in a correlation function of the sequence comprising the at least one temporal scaling of the sequence is reduced as compared to a side lobe in the correlation function which may maximally be acquired by different arrangements of the signal states in the sequence.

13. The device according to claim 12, wherein an order of the signal states within the at least one sequence is selected such that a sum which is based on side lobes of the correlation function of the sequence comprising the at least one temporal scaling of the sequence is reduced as compared to a sum which may maximally be acquired by different arrangements of the signal states in the sequence, wherein the sum is based on side lobes resulting from the different arrangements, and/or wherein the order of the signal states within the at least one sequence is selected such that a greatest side lobe of the correlation function of the sequence comprising the at least one temporal scaling of the sequence is reduced as compared to a greatest side lobe which may maximally be acquired by different arrangements of the signal states in the sequence.

14. The device according to claim 13, wherein the sum which is based on the side lobes is below a first threshold value, and/or wherein the greatest side lobe is below a second threshold value.

15. The device according to claim 14, wherein the first threshold value corresponds to a second-lowest sum which is based on side lobes of correlation functions of possible sequences and/or wherein the second threshold value corresponds to a greatest side lobe of a sequence comprising a second-lowest greatest side lobe of the correlation functions.

16. The device according to claim 12, wherein the sequence corresponds to a unipolar sequence.

17. A method for providing information on at least one sequence, wherein the at least one sequence describes temporally successive signal states, the method comprising receiving information on a number of the signal states, generating a plurality of possible sequences based on the information on the number of the signal states, calculating correlation functions between a sequence and at least one temporal scaling of the sequence for at least one subset of the possible sequences, wherein a correlation function includes a main lobe and one or several side lobes, determining the at least one sequence based on the correlation functions, wherein the order of the signal states within the at least one sequence is selected such that a side lobe in a correlation function of the sequence comprising the at least one temporal scaling of the sequence is reduced as compared to a side lobe which may maximally be acquired in a correlation function by different arrangements of the signal states in the sequence, and determining the information on the at least one sequence based on the at least one sequence, and providing the information on the at least one sequence.

* * * * *